(12) United States Patent
Johnson

(10) Patent No.: US 10,398,664 B2
(45) Date of Patent: Sep. 3, 2019

(54) METHODS OF DIAGNOSING AND TREATING INFECTED IMPLANTS

(71) Applicant: Lanny Leo Johnson, Frankfort, MI (US)

(72) Inventor: Lanny Leo Johnson, Frankfort, MI (US)

(*) Notice: Subject to any disclaimer, the term of this patent is extended or adjusted under 35 U.S.C. 154(b) by 0 days.

(21) Appl. No.: 16/058,909

(22) Filed: Aug. 8, 2018

(65) Prior Publication Data

US 2019/0000786 A1 Jan. 3, 2019

Related U.S. Application Data

(60) Continuation-in-part of application No. 15/787,343, filed on Oct. 18, 2017, now Pat. No. 10,143,670, which is a division of application No. 15/484,827, filed on Apr. 11, 2017, now Pat. No. 10,016,380, which is a continuation-in-part of application No. 15/189,510, filed on Jun. 22, 2016, now Pat. No. 9,925,152, which is a division of application No.
(Continued)

(51) Int. Cl.
| | |
|---|---|
| A61K 31/192 | (2006.01) |
| A61K 8/60 | (2006.01) |
| A61Q 17/00 | (2006.01) |
| A61K 8/34 | (2006.01) |
| A61K 31/352 | (2006.01) |
| A61K 31/7048 | (2006.01) |
| A61K 31/11 | (2006.01) |
| A23L 3/3481 | (2006.01) |
| A61L 2/18 | (2006.01) |
| A61L 15/44 | (2006.01) |
| A61K 9/127 | (2006.01) |
| A61K 9/08 | (2006.01) |
| A61K 9/00 | (2006.01) |
| A01N 31/02 | (2006.01) |
| A23L 3/349 | (2006.01) |
| A23L 3/3508 | (2006.01) |
| A01N 35/04 | (2006.01) |
| A23L 3/3544 | (2006.01) |
| A01N 37/40 | (2006.01) |
| A01N 43/16 | (2006.01) |
| A23B 7/154 | (2006.01) |
| A61K 8/14 | (2006.01) |
| A61K 45/06 | (2006.01) |
| A61Q 19/08 | (2006.01) |
| A61K 8/368 | (2006.01) |
| A61L 2/22 | (2006.01) |

(52) U.S. Cl.
CPC ........... *A61K 31/192* (2013.01); *A01N 31/02* (2013.01); *A01N 35/04* (2013.01); *A01N 37/40* (2013.01); *A01N 43/16* (2013.01); *A23B 7/154* (2013.01); *A23L 3/349* (2013.01); *A23L 3/3481* (2013.01); *A23L 3/3508* (2013.01); *A23L 3/3544* (2013.01); *A61K 8/14* (2013.01); *A61K 8/347* (2013.01); *A61K 8/368* (2013.01); *A61K 8/602* (2013.01); *A61K 9/0009* (2013.01); *A61K 9/0014* (2013.01); *A61K 9/0019* (2013.01); *A61K 9/08* (2013.01); *A61K 9/127* (2013.01); *A61K 31/11* (2013.01); *A61K 31/352* (2013.01); *A61K 31/7048* (2013.01); *A61K 45/06* (2013.01); *A61L 2/18* (2013.01); *A61L 2/22* (2013.01); *A61L 15/44* (2013.01); *A61Q 17/005* (2013.01); *A61Q 19/08* (2013.01); *A23V 2002/00* (2013.01); *A61K 2300/00* (2013.01); *A61L 2202/21* (2013.01); *A61L 2300/404* (2013.01); *Y02A 50/473* (2018.01); *Y02A 50/478* (2018.01)

(58) Field of Classification Search
None
See application file for complete search history.

(56) References Cited

U.S. PATENT DOCUMENTS

| | | |
|---|---|---|
| 4,880,416 A | 11/1989 | Horiuchi et al. |
| 4,997,850 A | 3/1991 | Kimura et al. |

(Continued)

FOREIGN PATENT DOCUMENTS

| | | |
|---|---|---|
| CN | 102048481 A | 5/2011 |
| CN | 104072362 A * | 10/2014 |

(Continued)

OTHER PUBLICATIONS

Almeida, Ana Amelia P., et al., "Antibacterial Activity of Coffee Extracts and Selected Coffee Chemical Compounds against Enterobacteria," *J. Agric. Food Chem.*, 54:8738-8743 (2006).

(Continued)

*Primary Examiner* — Celeste A Roney
(74) *Attorney, Agent, or Firm* — Brinks Gilson & Lione; Ryan L. Marshall

(57) ABSTRACT

The present invention relates to methods for treating microbial infections on the surfaces of an implant or other surfaces near an implant in a patient. In particular, the methods are useful for treating biofilm infections. The methods include the use of minimally invasive techniques, including the use of ultra sound for facilitating the detection of biofilm infections on the implant or other surface of a patient and destroying the infection by administering an anthocyanin or an anthocyanidin or metabolite thereof. In particular, the administration of protocatechuic acid (PCA) or 2,4,6 trihydroxybenzaldehyde (2,4,6 THBA) for the treatment of an infected implant or other surface of a patient is described herein.

27 Claims, 27 Drawing Sheets

Related U.S. Application Data

14/264,553, filed on Apr. 29, 2014, now Pat. No. 9,498,413.

(60) Provisional application No. 61/818,275, filed on May 1, 2013.

(56) References Cited

U.S. PATENT DOCUMENTS

| | | | |
|---|---|---|---|
| 5,403,587 | A | 4/1995 | McCue et al. |
| 5,496,306 | A | 3/1996 | Engelhardt et al. |
| 5,597,598 | A | 1/1997 | van Rijn et al. |
| 6,123,679 | A | 9/2000 | Lafaut et al. |
| 6,770,039 | B2 | 8/2004 | Zhong et al. |
| 8,236,492 | B2 | 8/2012 | McDonnell et al. |
| 8,993,006 | B2 | 3/2015 | Hines et al. |
| 2003/0069317 | A1 | 4/2003 | Seitz, Jr. et al. |
| 2005/0100622 | A1 | 5/2005 | Nair et al. |
| 2006/0293258 | A1 | 12/2006 | Rohdewald |
| 2007/0020364 | A1 | 1/2007 | Burnett et al. |
| 2008/0033329 | A1 | 2/2008 | Downs et al. |
| 2008/0234618 | A1 | 9/2008 | Baldock |
| 2009/0163964 | A1* | 6/2009 | Boyden .......... A61L 2/0011 607/3 |
| 2009/0291944 | A1 | 11/2009 | Ash et al. |
| 2009/0304885 | A1 | 12/2009 | Perry |
| 2010/0004469 | A1 | 1/2010 | Shigehara et al. |
| 2010/0029574 | A1 | 2/2010 | Marini |
| 2010/0160838 | A1* | 6/2010 | Krespi ............ A61B 18/26 601/15 |
| 2010/0204204 | A1 | 8/2010 | Zaworotko et al. |
| 2011/0104243 | A1 | 5/2011 | Singhal |
| 2011/0264032 | A1* | 10/2011 | Rontal ............ A61B 17/22 604/22 |
| 2011/0268825 | A1 | 11/2011 | Burgos et al. |
| 2013/0231302 | A1 | 9/2013 | Raad et al. |
| 2014/0328902 | A1 | 11/2014 | Johnson |
| 2015/0011928 | A1 | 1/2015 | Burnett |

FOREIGN PATENT DOCUMENTS

| | | |
|---|---|---|
| CN | 105647674 A | 6/2016 |
| JP | 2010-184900 A | 8/2010 |
| WO | WO 00/047045 A1 | 8/2000 |
| WO | WO 2008/126980 A1 | 10/2008 |
| WO | WO 2009/003899 A1 | 1/2009 |
| WO | WO 2010/036930 A1 | 4/2010 |

OTHER PUBLICATIONS

Alves, M.J., et al., "Antimicrobial activity of phenolic compounds identified in wild mushrooms, SAR analysis and docking studies," *Journal of Applied Microbiology*, ISSN 1364-5072, 115:346-357 (2013).

Chao, Che-Yi, et al., "Antibacterial Effects of Roselle Calyx Extracts and Protocatechuic Acid in Ground Beef and Apple Juice," *Foodborne Pathogens and Disease*, vol. 00, No. 00, pp. 1-7 (2008).

Connors, Bret A., et al., "Comparison of Tissue Injury from Focused Ultrasonic Propulsion of Kidney Stones Versus Extracorporeal Shock Wave Lighotripsy," *J. Urol.*, 191(1):235-241 (2014).

Cuckler, JM, et al., "Diagnosis and management of the infected total joint arthroplasty," *The Orthopedic Clinics of North America*, 22(3):523-530, Abstract only (1991).

De Vita, Daniela, et al., "Activity of caffeic acid derivatives against Candida albicansbiofilm," *Bioorganic & Medicinal Chemistry Letters*, 24(6):1502-1505 (2014).

Della Valle, C.J., et al., "Preoperative testing for sepsis before revision total knee arthroplasty," *J Arthroplasty*, 22(6 Suppl 2):90-93, Abstract only (2007).

Donlan, R M, "Biofilms: Microbial life on surfaces," *Emerging Infectious Diseases*, EID, Atlanta, GA, US, 8(9): 881-890 (2002).

El Maghraby, G., "Skin delivery of 5-fluorouracil from ultradeformable and standard liposomes in vitro," *Journal of Pharmacy and Pharmacology*, 53:1069-1077 (2001).

Friedman, et al., "Antibacterial Activities of Phenolic Benzaldehydes and Benzoic Acids against Camylobacter jejuni, *Escherichia coli*, *Listeria monocytogenes*, and *Salmonella enterica*," *Journal of Food Protection*, 66(10):1811-1821 (2003).

Granick, Mark S., et al., "Direct-Contact Low-Frequency Ultrasound Clearance of Biofilm from Metallic Implant Materials," *Eplasty*, vol. 17, e13 (2017).

Gu, Zheng-yi, "Effect of pomegranate peel polyphenol gel on cutaneous wound healing in alloxan-induced diabetic rats," *Chinese Medical Journal*, 126(9):1700-1706 (2013).

Gutierrez, Sergio, et al., "The Usefulness of Non-Toxic Plant Metabolites in the Control of Bacterial Proliferation", *Probiotics and Antimicrobial Proteins*, New York, NY; Heidelberg: Springer, New York, NY ; Heidelberg : Springer, 9(3):323-333 (2017).

Hiebert, John M., et al., "The Immediate and Delayed Post-Debridement Effects on Tissue Bacterial Wound Counts of Hypochlorous Acid Versus Saline Irrigation in Chronic Wounds," *Eplasty*, vol. 16, e32 (2016).

International Search Report from corresponding International Application No. PCT/US2014/035881, 4 pages, dated Nov. 3, 2014.

Jayaraman, P., et al., "Activity and interactions of antibiotic and phytochemical combinations against Pseudomonas aeruginosa in vitro," *International Journal of Biological Sciences*, 6(6):556-568 (2010).

Kakkar, S., et al., "A Review on Protocatechuic Acid and Its Pharmacological Potential," Hindawi Publishing Company, *ISRN Pharmacology*, vol. 2014, article ID 952943, 9 pages.

Lingeman, James E., et al., "Shock wave lithotripsy: advances in technology and technique," *Nat Rev Urol.*, 6(12):660-670 (2009).

Liu, Keh-sen, et al., "In vitro Antibacterial Activity of Roselle Calyx and Protocatechuic Acid," *Phytotherapy Research*, 19:942-945 (2005).

Manfreda, F., et al., "New trends for diagnosis and treatment of infected total knee arthroplasty," *J Orthop Trauma Surg Rel Res*, 12(2):21-24 (2017).

Mariani, BD, et al., "Advances in the diagnosis of infection in prosthetic joint implants," *Mol Med Today*, 4(5):207-213, Abstract only (1998).

Meermans, Geert, et al., "Is There a Role for Tissue Biopsy in the Diagnosis of Periprosthetic Infection?" *Clin Orthop Relat Res*, 468:1410-1417 (2010).

Moran, A., et al., "Non-toxic plant metabolites regulate *Staphylococcus* viability and biofilm formation: a natural therapeutic strategy useful in the treatment and prevention of skin infections," *Biofouling: The Journal of Bioadhesion and Biofilm Research*, 30(10):1175-1182 (2014).

Nichol, Peter M., et al., "Noninvasive Assessment of Mitral Insufficiency by Transcutaneous Doppler Ultrasound," *Circulation*, 54(4):656-661 (1976).

Nizamutdinova, I.T., et al., "Anthocyanins from black soybean seed coats stimulate wound healing in fibroblasts and keratinocytes and prevent inflammation in endothelial cells," *Food and Chemical Toxicology*, 47:2806-2812 (2009).

Overhage, Joerg, et al., "Human Host Defense Peptide LL-37 Prevents Bacterial Biofilm Formation," *Infection and Immunity*, 76(9):4176-4182 (2008).

Panousis, K., et al., "Poor predictive value of broad-range PCR for the detection of arthroplasty infection in 92 cases," *Acta Orthop*, 76(3): 341-346, Abstract only (2005).

Parvizi, Javad, et al., "Diagnosis of Infected Total Knee," *Clin Orthop Relat Res*, 466:2628-2633 (2008).

Proestos, C., et al., "Analysis of flavonoids and phenolic acids in Greek aromatic plants: Investigation of their antioxidant capacity and antimicrobial activity," *Food Chemistry*, 95:664-671 (2006).

Scazzocchio, B., et al., "Cyanidin-3-O-β-Glucoside and Protocatechnuic Acid Exert Insulin-Like Effects by Upregulating PPARγ Activity in Human Omental Adipocytes," *Diabetes*, 60(9):2234-2244 (Sep. 2011).

(56) References Cited

OTHER PUBLICATIONS

Scher, David M., et al., "The predictive value of indium-III leukocyte scans in the diagnosis of infected total hip, knee, or resection arthroplasties," *The Journal of Arthroplasty*, 15(3):295-300, Abstract only (2000).

Semaming, Yoswaris, et al., "Pharmacological Properties of Protocatechuic Acid and Its Potential Roles as Complementary Medicine," *Evidence-Based Complementary and Alternative Medicine*, vol. 2015, 11 pages.

Sivamani, R.K., et al., "Phytochemicals and Naturally Derived Substances for Wound Healing," *Advances in Wound Care*, 1(5):213-217 (Oct. 2012).

Trampuz, Andrej, et al., "Sonication of Removed Hip and Knee Prostheses for Diagnosis of Infection," *N Engl J Med*, 357:654-663 (2007).

Uberos, J., et al., "Phenolic acid content and antiadherence activity in the urine of patients treated with cranberry syrup (Vaccinium macrocarpon) vs. trimethoprim for recurrent urinary tract infection," *Journal of Functional Foods*, 18:608-616 (2015).

Yee, Dennis KH, et al., "Review article: Joint aspiration for diagnosis of periprosthetic infection," *Journal of Orthopaedic Surgery*, 21(2):236-240 (2013).

Zillich, O.V., et al., "Release and in vitro skin permeation of polyphenols from cosmetic emulsions," *International Journal of Cosmetic Science*, 35(5):491-501 (2013).

\* cited by examiner

Minimum, maximum and optimum pH for growth of certain procaryotes.

| Organism | Minimum pH | Optimum pH | Maximum pH |
|---|---|---|---|
| Thiobacillus thiooxidans | 0.5 | 2.0-2.8 | 4.0-6.0 |
| Sulfolobus acidocaldarius | 1.0 | 2.0-3.0 | 5.0 |
| Bacillus acidocaldarius | 2.0 | 4.0 | 6.0 |
| Zymomonas lindneri | 3.5 | 5.5-6.0 | 7.5 |
| Lactobacillus acidophilus | 4.0-4.6 | 5.8-6.6 | 6.8 |
| Staphylococcus aureus | 4.2 | 7.0-7.5 | 9.3 |
| Escherichia coli | 4.4 | 6.0-7.0 | 9.0 |
| Clostridium sporogenes | 5.0-5.8 | 6.0-7.6 | 8.5-9.0 |
| Erwinia caratovora | 5.6 | 7.1 | 9.3 |
| Pseudomonas aeruginosa | 5.6 | 6.6-7.0 | 8.0 |
| Thiobacillus novellus | 5.7 | 7.0 | 9.0 |
| Streptococcus pneumoniae | 6.5 | 7.8 | 8.3 |
| Nitrobacter sp | 6.6 | 7.6-8.6 | 10.0 |

FIG. 1

| Organism | C. difficile 9689 | P.acnes 6919 | C.Prefringens 13124 | L. casei 393 | C.albicans | E. coli 8739 | |
|---|---|---|---|---|---|---|---|
| Amoxicillin | I/CZ/27 mm | I/CZ/36 mm | I/CZ/27 mm | I/CZ/27mm | NI/NZ | I/CZ/15mm | |
| Delphinidin | NI/NZ | I/NZ | I/CZ/8mm | I/NZ | NI/NZ | NI/NZ | |
| Pelargonidin | NI/NZ | I/CZ/1mm | I/CZ/9mm | NI/NZ | NI/NZ | NI/NZ | |
| Cyanidin Cl | I/NZ | NI/NZ | I/CZ/6mm | NI/NZ | NI/NZ | NI/NZ | |
| 28% C-3-G | NI/NZ | I/CZ/23 mm | NI/NZ | NI/NZ | N/i/NZ | I/NZ | |
| PCA | I/CZ/1mm | I/CZ/22 mm | I/CZ/5.5mm | I/CZ/5mm | I/CZ/0.5mm | I/CZ/4.5mm | |
| 246THBA | NI/NZ | NI/NZ | NI/NZ | I/NZ | I/CZ 4 mm | I/CZ/ 6 mm | |

| Organism | E. coli 43895 | S.aureus 6538 | S.aureus 33591 | S. mutans 25175 | S.pyogenes 19615 | P.aeruginosa 9027 | K. pneumonia 4352 |
|---|---|---|---|---|---|---|---|
| Amoxicillin | | I/CZ/13mm | I/CZ/24 mm | I/CZ/9mm | I/CZ/34mm | | NI/NZ |
| Delphinidin | | NI/NZ | I/CZ/10mm | I/CZ/7mm | I/NZ | | NI/NZ |
| Pelargonidin | | NI/NZ | I/CZ/3mm | I/CZ/4mm | NI/NZ | | NI/NZ |
| Cyanidin Cl | | NI/NZ | I/CZ/1mm | I/CZ/3mm | NI/NZ | | NI/NZ |
| 28% C-3-G | | I/CZ/0.3mm | I/NZ | I/CZ/4mm | I/NZ | I/NZ | I/CZ/1mm |
| PCA | I/CZ/9mm | I/CZ/8mm | I/CZ/9mm | I/CZ/1mm | I/CZ/2.5mm | I/CZ/10mm | I/CZ/1mm |
| 246THBA | I/CZ/3mm | I/CZ/13mm | I/C/14mmZ | I/CZ/2mm | I/CZ 3 mm | I/CZ/ 3 mm | I/CZ/6mm |

NI = No inhibition of growth
NZ = No zone
I = Inhibition
CZ = Clear zone

FIG. 6

2,4,6 Trihydroxybenzaldehyde In vitro Testing:

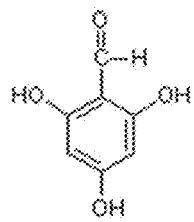

Interpretation of Results:

NZ / C = No zone was seen, however there was clearing of growth directly underneath the sample.

NZ / NC = No zone / No clearing of growth underneath the sample.

CZ = Clear zone

| SAMPLE ID | ORGANISM | ZONE OF INHIBITION |
|---|---|---|
| 1 | Aspergillus fumigatus   ATCC 1022 | NI /NZ |
|  | Clostridium difficile   ATCC 9689 | NI /NZ |
|  | Clostridium perfringens   ATCC 13124 | NI /NZ |
|  | Penicillium chrysogenum   ATCC 10134 | NI /NZ |
|  | Propionobacterium acnes   ATCC 6919 | NI /NZ |
|  | Streptococcus mutans   ATCC 25175 | I / CZ / 2 mm |
|  | Streptococcus pyogenes   ATCC 19615 | I / CZ / 3 mm |
|  | Trichophyton rubrum   ATCC 38484 | NI /NZ |

| SAMPLE ID | ORGANISM | ZONE OF INHIBITION |
|---|---|---|
| 1 | Candida albicans   ATCC 10231 | I / NZ |
|  | Lactobacillus casei   ATCC 393 | I / CZ / 4 mm |

FIG. 7

Zero Time: Control Group 1 (untreated and uninfected)
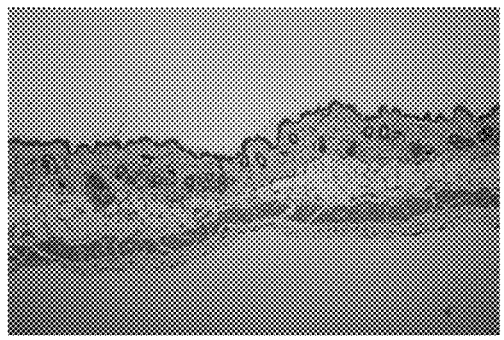 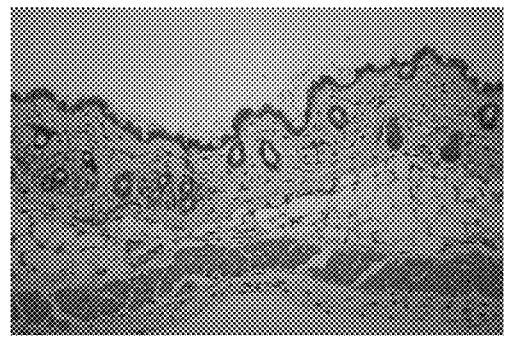
H&E X100
FIG. 14
H&E X200
FIG. 15
Two hours: Control Group 1 (untreated and uninfected)
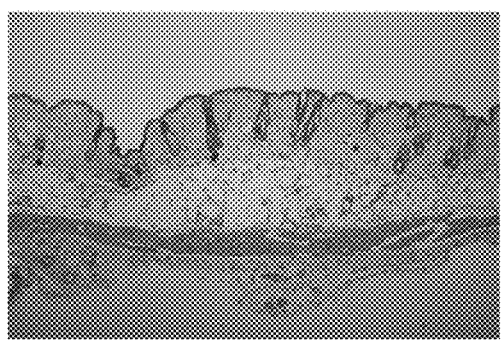 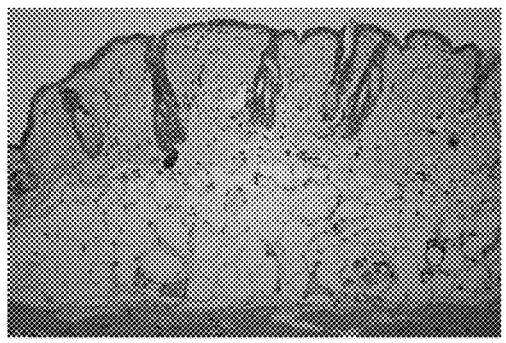
H&E X100
FIG. 16
H&E X200
FIG. 17

48 hours: Control Group 1 (untreated and uninfected)
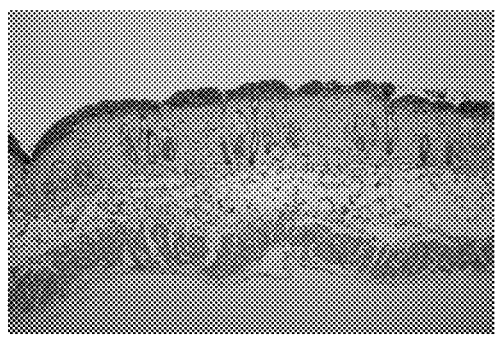 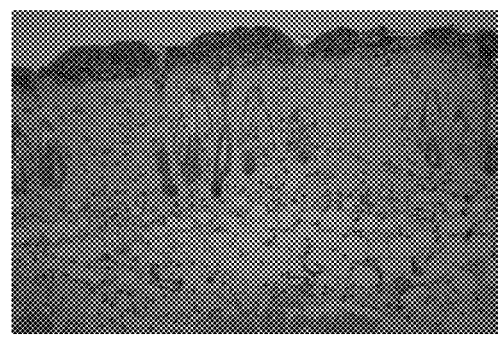
H&E X100
FIG. 18
H&E X 200
FIG. 19
2 hours: Control Group 2 (untreated and infected)
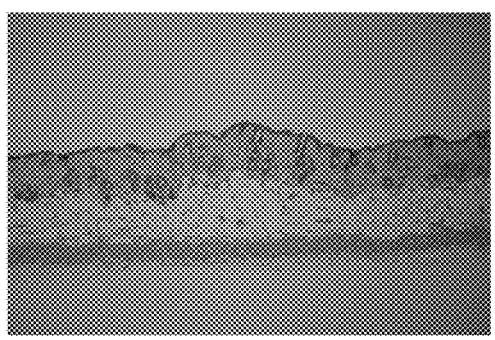 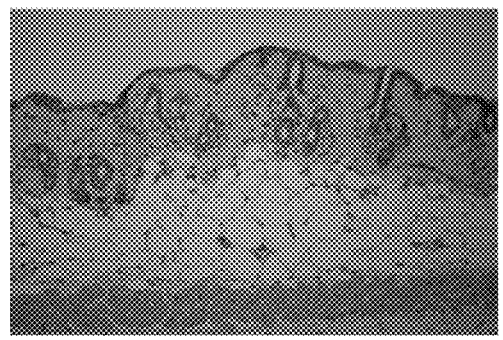
H&E X100 (2A)
FIG. 20
H&E X200 (2A)
FIG. 21

48 hours: Control Group 2 (untreated and infected)

H&E X100

H&E X200

48 hours: Experimental Group 1 (PCA 25 mM)

H&E X100 (9c)

H&E X200 (9c)

48 hours: Experimental Group (PCA 50 mM)

H&E X100 (5b)

H&E X200 (5b)

48 hours: Experimental Group (C3G 100 mM)

H&E X100 (19c)

H&E X200 (19c)

48 hours: Experimental Group (C3G 200 mM)

FIG. 32

Pseudomonas Results

10% Concentration not as Effective

|  | CFU / Coupon | Log Density |
|---|---|---|
| Cloth 2% | $1.2 \times 10^{10}$ | 10.5 |
| Cloth 2% | $1.6 \times 10^{10}$ | 10.6 |
| Cloth 10% | $1.4 \times 10^{10}$ | 10.6 |
| Cloth 10% | $8.9 \times 10^{9}$ | 10.4 |
| 3 ply 10% | $3.9 \times 10^{9}$ | 10.0 |
| 3 ply 10% | $4.5 \times 10^{9}$ | 10.1 |
| 5 ply 10% | $3.6 \times 10^{9}$ | 10.0 |
| 5 ply 10% | $6.9 \times 10^{8}$ | 9.3 |

- CFU: Colony Forming Units is estimation of # viable bacteria
- Coupon is the article of cloth or stainless steel mesh
- Log Density is calculation of biofilm present

FIG. 33

Pseudomonas Results

20% Concentration was Very Effective

|  | CFU / Coupon | Log Density |
|---|---|---|
| Cloth | $1.3 \times 10^2$ | 2.5 |
| Cloth | $1.0 \times 10^1$ | 1.4 |
| 3 ply metal | $< 1.0 \times 10^1$ | $< 1.4$ |
| 3 ply metal | $< 1.0 \times 10^1$ | $< 1.4$ |
| 5 ply metal | $< 1.0 \times 10^1$ | $< 1.4$ |
| 5 ply metal | $< 1.0 \times 10^1$ | $< 1.4$ |
| Glass slide | $7.1 \times 10^7$ | 8.3 |
| Glass slide | $7.5 \times 10^6$ | 7.3 |
| Crystals 3 ply | $< 1.0 \times 10^1$ | $< 1.4$ |
| Crystals 3 ply | $4.6 \times 10^3$ | 4.1 |
| Crystals 5 ply | $1.6 \times 10^6$ | 6.6 |
| Crystals 5 ply | $< 1.0 \times 10^1$ | $< 1.4$ |

FIG. 34

MRSA Results

20% not as Effective

|               | CFU / Coupon      | Log Density |
|---------------|-------------------|-------------|
| Cloth         | $2.0 \times 10^5$ | 5.7         |
| Cloth         | $2.2 \times 10^6$ | 6.8         |
| 3 ply metal   | $5.7 \times 10^7$ | 8.2         |
| 3 ply metal   | $7.9 \times 10^6$ | 7.3         |
| 5 ply metal   | $2.7 \times 10^4$ | 4.9         |
| 5 ply metal   | $2.2 \times 10^5$ | 5.8         |
| Glass slide   | $1.5 \times 10^7$ | 7.6         |
| Glass slide   | $2.2 \times 10^7$ | 7.8         |
| Crystals 3 ply| $4.6 \times 10^8$ | 9.1         |
| Crystals 3 ply| $3.0 \times 10^8$ | 8.9         |
| Crystals 5 ply| $5.7 \times 10^6$ | 7.2         |
| Crystals 5 ply| $9.8 \times 10^7$ | 8.4         |

FIG. 35

MRSA Results
30% Concentration Very Effective

| Sample ID | CFU on Coupon | Log Density | |
|---|---|---|---|
| 5. cloth | <1.0 x 10$^1$ | <1.4 | no colonies |
| 6. cloth | 7.1 x 10$^2$ | 3.3 | |
| 7. 3 ply SS | 1.2 x 10$^3$ | 3.5 | |
| 8. 3 ply SS | 2.4 x 10$^3$ | 3.8 | |
| 9. 5 ply SS | 3.2 x 10$^3$ | 3.9 | |
| 10. 5 ply SS | 2.3 x 10$^3$ | 3.8 | |

- Sample Size: 75mm x 25mm
- Culture Medium: R2A, Soybean Casein Digest Broth
- Neutralizer: Dey-Engley Broth
- Culture Media: Nutrient Agar
- Batch Phase: 6 Hours

- Continuous Flow Phase: 48 hours

CFU: Colony Forming Units is estimation of # viable bacteria
Coupon is the article of cloth or stainless steel mesh
Log Density is calculation of biofilm present

FIG. 36

Pseudomonas aeruginosa
Greater than 99.9% kill in 30 minutes

| Organism: Pseudomonas aeruginosa | | | ATCC: 700888 | |
|---|---|---|---|---|
| Initial Inoculum Concentration (CFU / 1.0 mL) | | | $1.3 \times 10^8$ | |
| | Glass Slide (Control) | | 30% PCA in 70% IPA | |
| CFU / Sample | Replicate 1 | Replicate 2 | Replicate 1 | Replicate 2 |
| 30 Minute Contact Time | $1.8 \times 10^{10}$ | $3.0 \times 10^{10}$ | $1.5 \times 10^4$ | $2.4 \times 10^7$ |
| 30 Minute Contact Time (Mean) | $2.4 \times 10^{10}$ | | $1.2 \times 10^7$ | |
| Log Reduction at 30 Minutes | 3.3 | | | |
| 60 Minute Contact Time | $2.5 \times 10^{10}$ | $2.2 \times 10^{10}$ | $2.4 \times 10^8$ | $3.0 \times 10^8$ |
| 60 Minute Contact Time (Mean) | $2.4 \times 10^{10}$ | | $1.5 \times 10^8$ | |
| Log Reduction at 60 Minutes | 2.2 | | | |

FIG. 37

MRSA
Greater than 90% kill in 30 minutes

| Organism: *Staphylococcus aureus* (MRSA) | | | ATCC: 33591 | |
|---|---|---|---|---|
| Initial Inoculum Concentration (CFU / 1.0 mL) | | | $2.1 \times 10^8$ | |
| | CFU / Sample | | | |
| | Glass Slide (Control) | | 30% PCA | |
| 30 Minute Contact Time | $6.9 \times 10^7$ | $5.0 \times 10^7$ | $2.7 \times 10^6$ | $3.2 \times 10^6$ |
| 30 Minute Contact Time (Mean) | $6.0 \times 10^7$ | | $3.0 \times 10^6$ | |
| Log Reduction at 30 Minute | 1.3 | | | |
| 60 Minute Contact Time | $2.3 \times 10^7$ | $2.7 \times 10^7$ | $1.7 \times 10^5$ | $3.8 \times 10^6$ |
| 60 Minute Contact Time (Mean) | $2.5 \times 10^7$ | | $2.0 \times 10^6$ | |
| Log Reduction at 60 Minute | 1.1 | | | |

FIG. 38

Pseudomonas aeruginosa
30% PCA Single Spray on Existing Biofilms

Inoculum on glass slide
10 million organisms

RESULTS
Log reduction with PCA at 30 minutes: 3.3
Log reduction with PCA at 60 minutes: 2.2
99.9% Reduction

FIG. 40

Staphylococcus aureus ATCC 33591
30% PCA Single Spray on Existing Biofilms

Inoculums on glass slide
10 million organisms allowed to grow

RESULTS
30 minutes: 60 million to 3 million
60 minutes: 25 million to 2 million
90% reduction

FIG. 41

Reagent Composite Comparisons
Number No Growth Culture Post Treatment

| Reagent | Aerobic | Anaerobic |
|---|---|---|
| Chloroprep | 21/23 | 19/23 |
| Betadine | 6/11 | 7/11 |
| 70% IPA | 16/23 | 12/23 |
| PCA* | 32/36 | 24/35 |

*Did not include 1% PCA results

FIG. 42

Result Summary
% of No Growth

| Reagent | Aerobic | Anaerobic |
|---|---|---|
| Chloroprep | 91% | 82% |
| Betadine | 55% | 64% |
| 70% IPA | 70% | 52% |
| PCA | 89% | 69% |

FIG. 43

METHODS OF DIAGNOSING AND TREATING INFECTED IMPLANTS

CROSS-REFERENCE TO RELATED APPLICATIONS

This application is a continuation-in-part of U.S. application Ser. No. 15/787,343, filed Oct. 18, 2017, which is a divisional application of U.S. application Ser. No. 15/484,827 filed Apr. 11, 2017, now U.S. Pat. No. 10,016,380, issued Jul. 10, 2018, which is a continuation-in-part of U.S. application Ser. No. 15/189,510, filed Jun. 22, 2016, now U.S. Pat. No. 9,925,152, issued Mar. 27, 2018, which is a divisional of U.S. application Ser. No. 14/264,553, filed Apr. 29, 2014, now U.S. Pat. No. 9,498,413, issued Nov. 22, 2016, which claims the benefit under 35 U.S.C. § 119(e) of U.S. Provisional Application No. 61/818,275, filed May 1, 2013, the disclosures of which are incorporated, in their entirety, by this reference.

FIELD OF THE INVENTION

The present invention relates to methods for treating microbial infections on the surfaces of an implant or other surfaces near an implant in a patient. In particular, the methods are useful for treating biofilm infections. The methods include using minimally invasive techniques such as ultra sound for facilitating the detection of biofilm infections on an implant or other surface of a patient and destroying the infection by administering an anthocyanin or an anthocyanidin or metabolite thereof. In particular, the administration of protocatechuic acid (PCA) or 2,4,6 trihydroxybenzaldehyde (2,4,6 THBA) for the treatment of an infected implant or other surface of a patient is described herein.

BACKGROUND OF THE INVENTION

Post-operative infections of implants, such as total joint implants following surgery is frequent, occurring in 1-2% of all cases. The present diagnosis of infected surgical and medical implants is not always successful. The clinical presentation is often problematic. Presently, diagnosis depends on both clinical judgment and reliance on standard serologic clinical tests. These tests include sedimentation rate (ESR), C-reactive protein (CRP), white blood cell count (WBC), analysis of aspirated joint fluid, and interpretation of intraoperative tissue and fluid test results. Even having evidence of implant loosening stemming from x-ray identification and pre-operative needle aspirations can be negative for microbes and cultures of adjacent tissue at the time of surgery may be negative for any bacteria. Diagnosis, therefore, can be complicated and based on a combination of findings, rather than a single one. Even with these available diagnostic tests, an infected implant often escapes detection. Clinically, the presentation may not be evident and currently, there is no single or combination of tests accurate enough to diagnose an infected implant.

The many various methods may fail to identify the source of the infection in spite of clinical evaluation, laboratory testing, radiological scans and even molecular biology. One of the main reasons for difficulty in diagnosis is due to biofilm formation. Common biofilms stem from pathogenic bacteria and yeast. The biofilm forms a firm attachment to the implant that resists mobilization. Recently, it has been reported that the only way to mobilize these biofilms is after surgical removal of the prosthesis and subjection of the removed implant to ultrasound (see Trampuz et al., *NEJM.* 357, pp. 654-663, 2007).

Once an implant is diagnosed as being infected, there are few good treatment options. Traditional treatments include antibiotic therapy, irrigation, debridement, arthrodesis and even amputation in life threatening situations. Commonly, the treatment of an infected implant is surgical removal, placement of a temporary antibiotic impregnated spacer, followed by one or more surgeries to replace another implant with the attendant risks and morbidity. Thus, patients having an infection often require complex and expensive treatment that often has low outcome. Each of these methods are either unsuccessful or are met with complications. The humanitarian and societal costs are high for the diagnosis and treatment of loose and or infected total joints. These costs start with the initial diagnostic dilemmas that delay definitive treatment or result in erroneous therapies. There is, therefore, an unmet need for more effective methods of diagnosing an infected implant that is in a patient and treating the infected implant. Described herein are effective methods for detecting an infection of an implant and compounds and compositions for treating the infected implant that solves this unmet need.

SUMMARY OF THE INVENTION

In its various embodiments, the present invention relates to methods for treating infections (e.g., bacterial infections) on the surfaces of an implant in a patient. In particular, the methods are useful for treating biofilm infections (e.g., biofilm bacterial infections). The methods include the use of minimally invasive techniques for determining the presence of an infection on the implant and destroying the infection by administering an anthocyanin or an anthocyanidin or metabolites thereof (e.g., protocatechuic acid or 2,4,6 trihydroxybenzaldehyde).

In one embodiment, a method of treating a biofilm bacterial infection on a surface of an implant or a surface of a patient suspected of having a biofilm bacterial infection is disclosed. The method includes removing a biofilm-forming bacteria by a minimally invasive technique comprising needle aspiration or an application of ultrasound or both to determine a presence of a biofilm around or on the surface of the implant or surface of the patient, wherein the minimally invasive technique dislodges the biofilm colony; and inhibiting or destroying the biofilm colony and all biofilm-forming bacteria on or around the surface of the implant in the patient or surface of the patient by administering a composition comprising protocatechuic acid or 2,4,6-trihydroxybenzaldehyde or a mixture or combination thereof or administering pure crystals or a powder of protocatechuic acid or 2,4,6-trihydroxybenzaldehyde or a mixture or combination thereof in an amount effective to inhibit or destroy the biofilm on or about the surface of the implant in the patient or the surface of the patient.

In some embodiments, the ultrasound is applied at a frequency and power sufficient to dislodge the biofilm-forming bacteria off the surface of the implant in a patient or the surface of the patient. In some embodiments, the minimally invasive technique is needle aspiration. In some embodiments, the minimally invasive technique is needle aspiration and application of ultrasound. In some embodiments, the ultrasound is applied prior to performing a first needle aspiration. In some embodiments, the ultrasound is applied after performing a first needle aspiration. In some embodiments, the surface of the patient is a closed wound, intact skin or skin having a sinus track.

In some embodiments, the implant is a medical device, a medical or surgical implant, total joint prosthesis, a catheter, a dental implant, or a heart or vascular graft. In some embodiments, a presence of the biofilm on the surface of the implant in the patient or the surface of the patient in previously negative tests for a biofilm-forming bacteria following needle aspiration requires application of ultrasound to dislodge the biofilm colony and biofilm-forming bacteria for confirmation of the presence of the biofilm on the surface of the implant in the patient or surface of the patient. In some embodiments, the ultrasound is applied by a transcutaneous probe, external stimulation, or lithotripsy. In some embodiments, a presence of the biofilm on the surface is determined by a needle aspiration prior to the application of the composition or the crystals.

In some embodiments, the biofilm comprises a biofilm-forming bacteria selected from *Pseudomonas aeruginosa* and Methicillin-resistant *Staphylococcus aureus*.

In some embodiments, the composition is a solution comprising protocatechuic acid or 2,4,6-trihydroxybenzaldehyde or a mixture or combination thereof. In some embodiments, the solution comprises about 0.25% to about 50% by weight of protocatechuic acid or 2,4,6-trihydroxybenzaldehyde or a mixture or combination thereof. In some embodiments, the solution comprises about 20% to about 30% by weight of protocatechuic acid or 2,4,6-trihydroxybenzaldehyde or a mixture or combination thereof.

In some embodiments, the composition, powder, or the crystals is administered once. In some embodiments, the composition, powder, or crystals is administered continuously, hourly, daily, weekly, or monthly.

In some embodiments, ultrasound is applied to or near the surface of the implant or surface of the patient having the biofilm bacterial infection to dislodge the biofilm colony and facilitate release of a biofilm-forming bacteria from the surface. In some embodiments, an aspirate obtained from performing the needle aspiration is cultured to determine if any biofilm-forming bacteria are present, thereby indicating a presence of the biofilm bacterial infection on the surface of the implant or the surface of the patient. In some embodiments, an aspirate obtained from performing the needle aspiration is cultured to determine if any biofilm forming bacteria are present on the surface of the implant or the surface of the patient following administration of the composition or the crystals.

In some embodiments, the ultrasound is applied at a frequency of about 10 kHz to about 60 kHz. In some embodiments, the ultrasound is applied at a power density of about 0.1 W/cm$^2$ to about 0.5 W/cm$^2$. In some embodiments, the ultrasound is applied at a frequency of about 40 kHz and a power density of about 0.22 W/cm$^2$. In some embodiments, the ultrasound is applied percutaneously and transcutaneously. In some embodiments, the surface is further washed with a physiologically compatible solution to facilitate release of a biofilm-forming bacteria. In some embodiments, the surface is washed with a composition comprising an anti-microbial peptide.

In one aspect, a method of treating a biofilm bacterial infection on a surface of an implant or a surface of a patient suspected of having a biofilm bacterial infection, is disclosed including a) performing a needle aspiration to determine a presence of a biofilm-forming bacteria around or on the surface of the implant or surface of the patient; b) culturing the biofilm-forming bacteria obtained from the needle aspiration to determine a presence of the biofilm-forming bacteria around or on the surface of the implant or surface of the patient; c) if the culture is negative, then an ultrasound is applied to dislodge the biofilm colony and biofilm-forming bacteria from the surface of the implant or the surface of the patient; d) if the culture is identified as positive, then administering to a surrounding space in proximity of the surface of the implant or the surface of a patient a solution comprising protocatechuic acid or 2,4,6-trihydroxybenzaldehyde or a mixture or combination thereof in an amount of about 0.25% to about 50% by weight or administering crystals of protocatechuic acid or 2,4,6-trihydroxybenzaldehyde or a mixture or combination thereof, which is effective to inhibit or destroy the biofilm colony and all biofilm-forming bacteria on the surface of the implant or the surface of the patient; and e) optionally applying ultrasound prior to performing the needle aspiration to dislodge the biofilm colony and facilitate release of a biofilm forming bacteria from the surface; wherein the surface of the patient is a closed wound, intact skin or skin having minimal exposure with a fistula; and wherein the implant is a medical device, a medical or surgical implant, a dental implant, total joint prosthesis, a catheter, or a heart or vascular graft.

BRIEF DESCRIPTION OF THE DRAWINGS

FIG. 1 provides the minimum, maximum and optimum pH for growth of microorganisms. Acidic environments retard proliferation of various bacteria. Anthocyanins, anthocyanidins and main metabolites are unstable relative to basic pH; thus, anthocyanins, anthocyanidins and main metabolites thereof have the potential to lower the pH of wound tissue as well as any surfaces and act as bactericidal or bacteriostatic.

FIG. 6 is a table providing a summary of the effectiveness of certain anthocyanins, anthocyanidins and a metabolite, including bactericidal or bacteriostatic activity. During this test, the purity, concentrations and molecular weight of these test substances (compounds) were known. The carrier was water and the dose was accurately calculated. Delphinidin limited growth against *C. perfringens*, *S. aureus*, and MRSA. Pelargonidin limited growth of *P. acnes*, *C. perfingens*, *S. aureus*, MRSA, and *S. pyogenes*. Cyanidin CI was effective against *C. difficile*, *C. prefringens*, *S. aureus* ATCH 6538, *S. aureus* (MRSA) ATCH 33591, *S. mutans*, and *S. pyogenes*. A proprietary formulation of cyanidin-3-glucoside (approximately 28% C3G by weight) had limited effectiveness during this study (18-24 hours for aerobes; 48 hours for anaerobes (*C. albicans* and *L. casei*); however, this C3G formulation, was effective against *P. acnes*, *E. coli*, MRSA, *K. pneumoniae* and *P. aeruginosa*. Protocatechuic acid (PCA), the main metabolite from anthocyanins and anthocyanidins, was effective against all bacteria tested as well as *C. albicans* and *K. pneumonia*. Importantly for skin wound treatment, PCA was effective against *S. aureus* 6538 and 33591 (MRSA) and *P. aeruginosa*. PCA was also effective on *C. albicans*, which is important considering its ability to form biofilms and difficulty in treating *C. albicans* when existing with a catheter or implant.

FIG. 7 is a table summarizing in vitro test results of 2, 4, 6 Trihydroxybenzaldehyde and demonstrating its ability to act as an antimicrobial, including as a bactericidal or bacteriostatic. Specifically, 2,4,6 THBA was effective against *E. coli, K. pneumonia, P. aeruginosa, S. aureus* 6538 and 33591 (MRSA); further it was effective against a fungi, *Aureobasidium pullulans*, ATCC 15233.

FIG. 14 is a photographic image of a cross section of rodent skin.

FIG. 15 is a photographic image of a cross section of rodent skin.

FIG. 16 is a photographic image of a cross section of rodent skin.

FIG. 17 is a photographic image of a cross section of rodent skin.

FIG. 18 is a photographic image of a cross section of rodent skin.

FIG. 19 is a photographic image of a cross section of rodent skin.

FIG. 20 is a photographic image of a cross section of rodent skin.

FIG. 21 is a photographic image of a cross section of rodent skin.

FIG. 32 provides a chart studying the effectiveness of anthocyanin and anthocyanidin metabolites against various microbes, including *P. acnes, C. difficile, E. coli* 8739 and 43895, *S. Aureus* 6538, 33591, *P. Aeruginosa* 9027, MRSA 51625 and *Legionella* 43662, methicillin resistant *staphylococcus epidermis* (MRSE), including MRSE ATCC 51625, and others.

FIG. 33 provides a chart summarize results of testing PCA against *Pseudomonas* biofilm.

FIG. 34 provides a chart summarize results of testing PCA against *Pseudomonas* biofilm.

FIG. 35 provides a chart summarize results of testing PCA against MRSA biofilm.

FIG. 36 provides a chart summarize results of testing PCA against MRSA biofilm.

FIG. 37 provides a chart summarize results of testing PCA against *Pseudomonas* biofilm.

FIG. 38 provides a chart summarize results of testing PCA against MRSA biofilm.

FIG. 40 shows the results for a single spray of 30% PCA in isopropyl alcohol on 10 million biofilms colonies of *Pseudomonas aeruginosa*.

FIG. 41 shows the concentration of 30% has lesser effect on MRSA, but still 90%.

FIG. 42 provides a composite of the results based only for no growth cultures following treatment by each solution. *Note that the 1% PCA was not included.

FIG. 43 provides the summation percentages of "no growth."

DETAILED DESCRIPTION OF THE INVENTION DEFINITIONS

Figure 2:
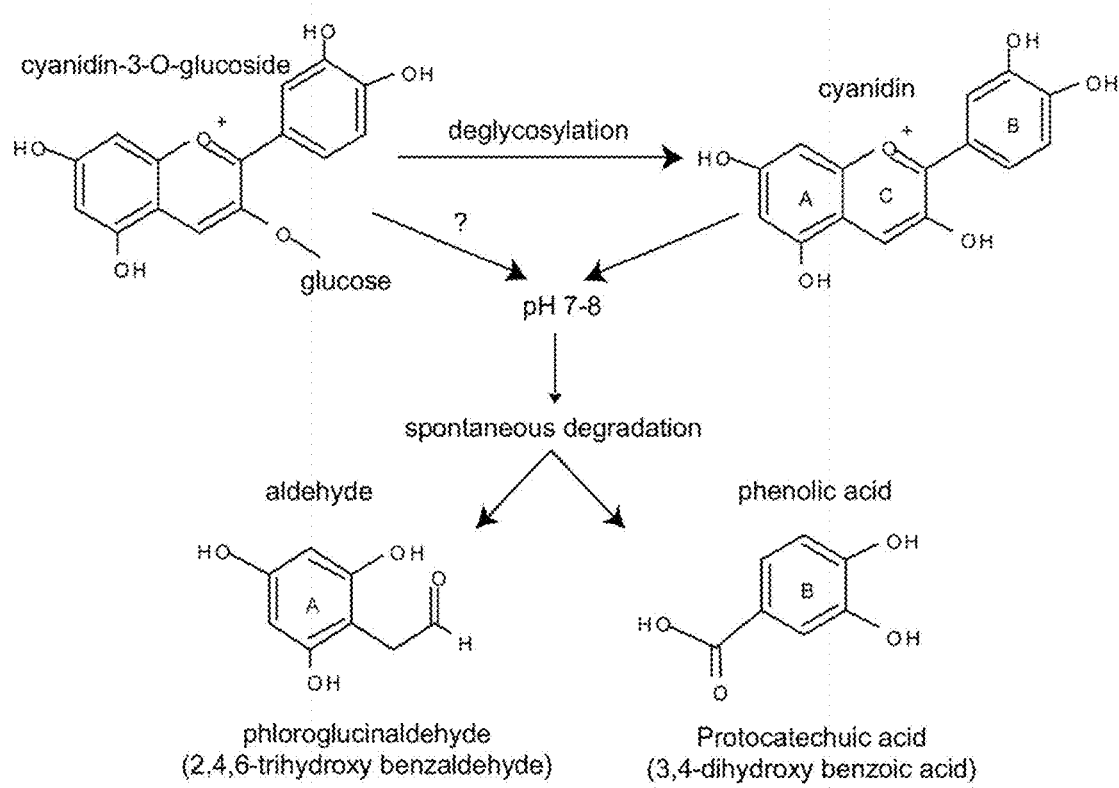
FIG. 2 is the metabolic pathway of cyanidin-3-glucoside (C3G) and includes the chemical structures of cyanidin-3-glucoside and cyanidin and their metabolites.
Figure 3:
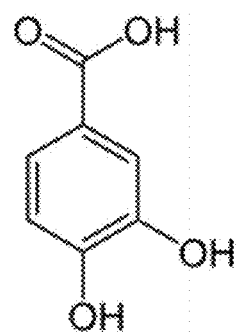
FIG. 3 is the chemical structure of Protocatechuic acid (PCA), a dihydroxybenzoic acid, a type of phenolic acid. It is a major metabolite of antioxidant polyphenols found in certain plants, including green tea.
Figure 4:
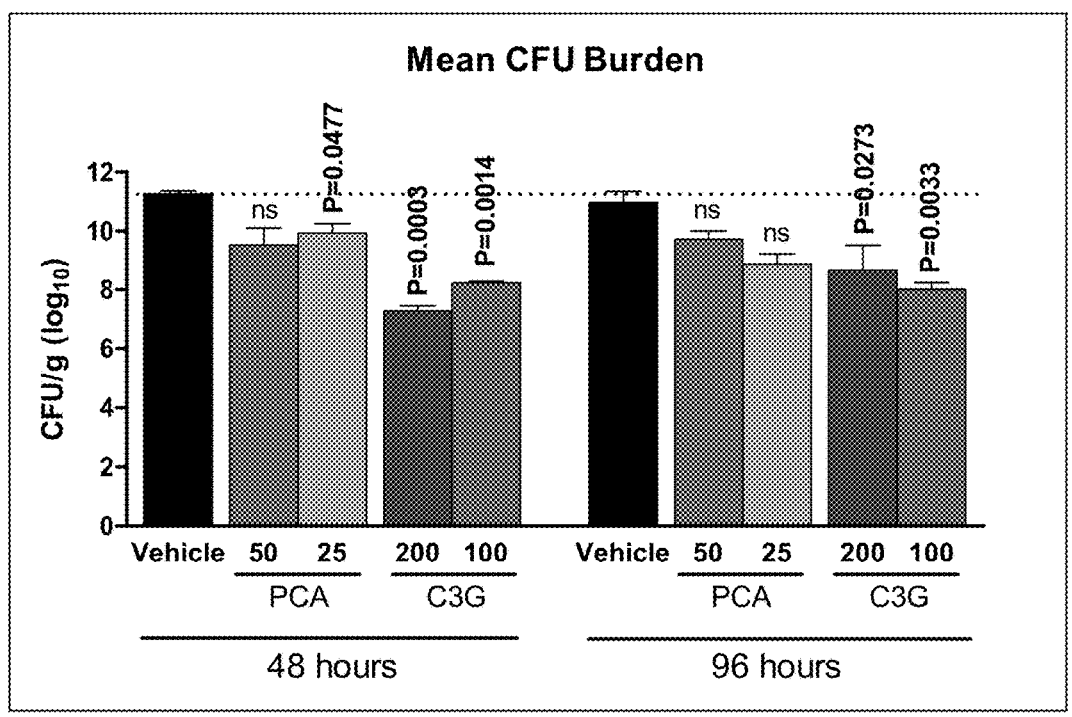
FIG. 4 compares concentrations of C3G and PCA to determine optimal effective concentrations. Bacterial burdens for *P. aeruginosa* were compared after treatment with C3G or PCA at 48 and 96 hours. A concentration of PCA 25 mM was effective to reduce the bioburden with statistical significance at 48 hours. C3G at 100 and 200 mM concentrations were effective at reducing the bioburden at 48 and 96 hours.
Figure 5:
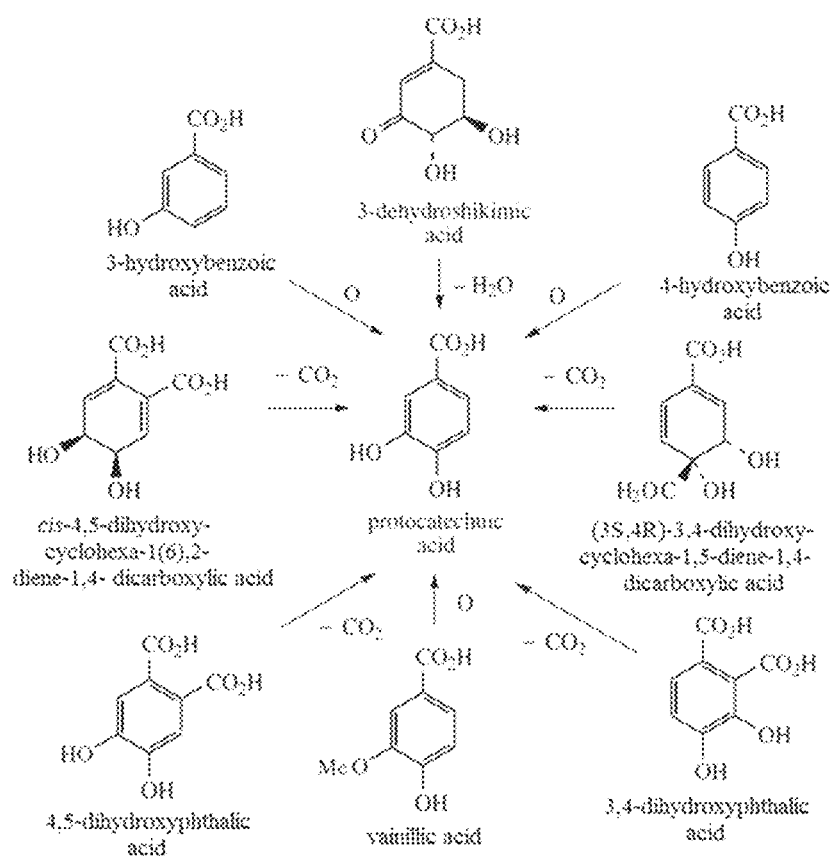
FIG. 5 is a chart disclosing potential sources of PCA.

Unless otherwise indicated, all technical and scientific terms used herein shall have the same meaning as is commonly understood by one of ordinary skill in the art to which the disclosed subject matter belongs. Unless otherwise indicated, the following definitions are applicable to this disclosure. All publications referred to throughout the disclosure are incorporated by reference in their entirety. To the extent any definition or usage provided by any document incorporated herein by reference conflicts with the definition or usage provided herein, the definition or usage provided herein controls.

As used in the specification and claims, the singular forms "a," "an," and "the" include plural referents unless the context clearly dictates otherwise. Thus, for example, reference to "a composition" includes mixtures or combinations of two or more such compositions.

Throughout the specification and claims, the word "comprise" and variations of the word, such as "comprising" and "comprises," means "including but not limited to," and is not intended to exclude, for example, other components, extracts, additives, or steps. It is also contemplated that embodiments described as "comprising" components, the invention also includes those same inventions as embodiments "consisting of" or "consisting essentially of."

Ranges can be expressed herein as "approximately" or from "about" one particular value, and/or to "about" another particular value. When such a range is expressed, another embodiment includes from the one particular value and/or to the other particular value.

A weight percent of a reagent, component, or compound unless specifically stated to the contrary, is based on the total weight of the reagent, component, composition or formulation in which the reagent, component, or compound is included, according to its usual definition.

By "reduce" or other forms of the word, such as "reducing" or "reduction," is meant decrease or lower a characteristic (e.g., inflammation, growth or viability of microorganisms, in particular biofilms).

By "promote" or other forms of the word, such as "promoting," is meant to induce a particular event or characteristic, or delay the development or progression of a particular event or characteristic, or to minimize the chances that a particular event or characteristic will occur.

"Treat" or other forms of the word, such as "treating," "treatment" or treated," is used here to mean to administer a composition or to perform a method in order to induce, reduce, eliminate, and prevent a characteristic (e.g., inflammation, growth or viability of microbes). It is generally understood that treating involves providing an effective amount of the composition to the mammal or surface (e.g., near a surface of an implant or patient) for treatment.

By the term "effective amount" of a composition or of a compound (e.g., PCA or 2,4,6 THBA) as provided herein is meant an amount sufficient to provide the desired benefit, either a reduction or prevention of microorganism growth or survival including biofilm colonies. As disclosed herein, the exact amount required will vary from use to use depending on a variety of processing parameters, as understood by one of ordinary skill, such as the type of surface, the type of microorganism to be treated, the surface size, the mode of delivery and the like.

The term "vehicle" or "vehicle carrier" as used herein refers to the manner in which the reagents or compositions may be delivered, including as a liquid, an injectable formulation, a solution, suspension, dispersion, and oral compositions and the like.

The term "growth factors" or "local growth factors" include but are not limited to, fibroblast growth factor (FGF), FGF-1, FGF-2, FGF-4, platelet-derived growth factor (PDGF), insulin-binding growth factor (IGF), IGF-1, IGF-2, epidermal growth factor (EGF), transforming growth factor (TGF), TGF-β, TGF-α, and collagen growth factors, and/or biologically active derivatives of these growth factors.

By "bactericidal" or "antimicrobial" is meant the ability to effect (e.g., eliminate, inhibit decrease, or prevent) microorganism growth, viability, and/or survival at any concentration. It also means to kill the microorganism. It is further meant to eliminate, inhibit, decrease, prevent, destroy, or kill a biofilm and/or biofilm-forming microorganisms.

By "bacteriostatic" is meant the ability to effect (e.g., stabilize or prevent future growth or prevent new growth) microorganism growth at any concentration. A bacteriostatic compound, agent or reagent does not eliminate or kill the bacteria.

By "antiseptic" is meant an antimicrobial reagent or composition that is applied to any surface, including skin or tissue, and particularly described herein on or around an implant or other surface of a patient near the implant to effect (e.g., eliminate, inhibit, decrease or prevent) microorganism growth, viability, and/or survival at any concentration. It is further meant to eliminate, inhibit, decrease, prevent, destroy, or kill a biofilm and/or biofilm-forming microorganisms.

By "disinfect" or other forms of the word, such as "disinfectant" or "disinfecting," is meant decrease or lower a characteristic (e.g., eliminate, reduce, inhibit, decrease, or prevent) microorganism growth, viability or survival at any concentration.

By "sanitize" or other forms of the word, such as "sanitizer" or "sanitizing," is meant decrease or lower a characteristic (e.g., eliminate, reduce, inhibit, decrease, or prevent) microorganism growth, viability or survival at any concentration. It is generally understood that sanitizing involves providing an effective amount of the composition to any surface (e.g., a surface of an implant or other surface of a patient near the implant).

By "sterilize" it is meant to kill microbes on the article being sterilized. Sterilize and sterilization include cold sterilization methods.

The term "ProC3G™" (commercially available Chroma-Dex®, Inc. Irvine, Calif. product) means a cyanidin 3-glucoside anthocyanin extracted from black rice and containing approximately 28% cyanidin 3-glucoside by weight with an additional 5% other anthocyanins.

Reference will now be made in detail to specific aspects of the disclosed materials, compounds, compositions, and methods, examples of which are illustrated in the following description and examples, and in the figures and their descriptions. Methods of Diagnosing and Treating Infected Implants and Surfaces of a Patient The present invention provides methods of diagnosing infected implants or other surfaces of a patient, compositions and uses for treating the infection on the surface of an inserted implant and other surfaces of a patient. More specifically, the methods and compositions described herein include the administration of an anthocyanin or an anthocyanidin or metabolites thereof, preferably protocatechuic acid (referred to herein as "PCA") and/or 2,4,6 trihydroxybenzaldehyde (referred to herein as "2,4,6 THBA") to inhibit or completely destroy a biofilm and all biofilm-forming microorganisms on or around a surface of an implant or of the patient.

The methods and compositions are used for the treatment of mammals, including humans. As described above, prior to the invention described herein there existed a great need for methods and compositions for diagnosing and treating infected implants. Accordingly, the methods and compositions described herein are suitable for the diagnosis and treatment of mammals having an infection on or around the surface of an implant. Such animals include equine, canine and feline.

Some embodiments of the invention described herein include methods of diagnosing whether an implant or other surface of a patient is infected with an infectious microorganism. In particular, the methods are suitable for detecting biofilm infections. The methods of diagnosing an infected implant or other surface of a patient are minimally invasive and may be carried out completely in an outpatient setting. Exemplary and non-limiting surfaces of the patient include a closed wound, intact skin, skin having a sinus track, or any surface of a patient (internal and external). Exemplary and non-limiting examples of implants include medical devices, a medical or surgical implant, total joint prosthesis, dental implants, a catheter, or a heart or vascular graft.

In some embodiments, the method for determining whether an implant is infected or surface of a patient is infected includes performing a needle aspiration biopsy to detect the presence of a bacterial infection on or around the surface of an implant. A needle biopsy is performed by aseptically preparing the skin lying above the area of the biopsy. Next, a needle is inserted into the skin and into the tissue overlying the implant or other internal surface of a patient and interstitial fluid is aspirated from the area surrounding the implant or area of infection on the surface of a patient. The biopsy may be guided by the use of additional imaging aids including fluoroscopic equipment, computed tomography, and or ultrasonography as is known in the art (see e.g., Yee et al., *Journal of Orthopaedic Surgery*, 21, pp. 236-240 (2013)).

In some embodiments, a physiologically compatible solution is utilized to irrigate the area surrounding the implant. These physiologically compatible solutions are well known in the art and include saline and Ringer's solution and the like. Irrigation of the surrounding tissue and implant may increase the likelihood of aspirating fluid containing an infectious microorganism. In addition, movement of the tissue, such as flexion, rotation and adduction of joints can be used to facilitate the aspiration of an infectious microorganism.

Exemplary devices for performing the needle aspiration include a needle attached to a housing for aspirating fluid from an area surrounding the implant suspected of having an infection. The aspiration device may include a connector for attaching a needle to the device and a plunger for extracting a sample of the joint fluid from the body of the patient through the needle into the housing of the device. The length and diameter of the needle depends upon the location of implant relative to the surface of the skin, accessibility of the implant, and ease of obtaining an aspirate. Suitable needles may be of a diameter ranging anywhere from 12 gauge to 30 gauge and from less than an inch in length to several inches in length as is necessary to reach the suspected area of infection or surface of an implant that is suspected to have an infection.

In some embodiments, the resulting needle aspiration biopsy of tissue surrounding the surface of the implant is cultured to identify the presence of any infectious microorganisms. The aspirate may be Gram stained to identify the presence of any bacteria microorganisms prior to culture.

In some embodiments, the aspirate is cultured to determine a presence of an infection. General bacteriological culturing methods are well known in the art. For example, aspirates can be inoculated on blood agar plates and grown for 24 to 48 hours under aerobic and anaerobic conditions. The presence of growth is monitored. Alternatively, aspirates can be inoculated in a growth broth, which is monitored for turbidity. The microorganism can be cultured for a day or for up to several weeks to maximize the possibility of detection. Prolonged culture periods can be more effective in identifying certain microorganisms including, for example, *Propionibacterium*, Bacilli, and *Peptostreptococcus* species. In addition, blood cultures may be utilized to aid in the detection of slow growing microorganisms. A positive culture necessitates treatment of the infected implant with an anthocyanin or anthocyanidin or metabolite thereof (e.g., PCA or 2,4,6 THBA) as further described herein.

In some embodiments, diagnosis of infection of an implant includes performing additional diagnostic assays, in addition to performing a minimally invasive needle aspiration biopsy technique. These include serologic tests including sedimentation rate (ESR) determination, C-reactive protein levels, white blood cell count, and neutrophil percentage. In addition, genetic analysis for the detection of microorganism genetic material may be performed using polymerase chain reaction (PCR) detection methods. Other clinical elements include, loss of function, onset of pain in the implant area, sinus tract, persistent wound drainage, or fever that may be indicative of an infection.

In some embodiments, the application of ultrasound is utilized to facilitate release of an infectious microorganism in situ. The application of ultrasound is described herein as particularly useful for detecting a biofilm infection present on or around an implant or other surface of a patient. With biofilm infections, it is not always possible to obtain a positive detection for the presence of pathogenic microorganisms because the microorganisms are in a quiescent non-growth stage and are enveloped in a thick extracellular matrix. Without being bound by any theory, it is thought that the application of ultrasound disrupts the structure of the extracellular matrix of the biofilm such that a biofilm-forming microorganism can be detected by any of the aforementioned methods. Ultrasound techniques for disrupting biofilms from implant materials in vitro is known in the art (see Granick et al., *Eplasty* 17(e13), pp. 128-134, 2017 and Trampuz et al., *NEJM* 357, pp. 654-663, 2007). These techniques have not been contemplated for disrupting a biofilm infection on an infected implant in situ or other surface of a patient in vivo. As first described herein, ultrasound energy can be applied in vivo to facilitate the release of any biofilm-forming microorganisms present on an infected implant or other surface of a patient.

Conventionally, ultrasound energy has been utilized for moving and ablating kidney stones through the technique of shock wave lithotripsy (see e.g., U.S. Pat. Nos. 5,496,306, 6,770,039 and 6,123,679). Suitable devices for performing lithotripsy include electrohydraulic, piezoelectric, and electromagnetic lithotripters, such as those available from Dornier Med Tech, Xi Xin Medical Instruments Co. Ltd, and Tissue Regeneration Technologies (see also e.g., Connors et al., *J Urol.* 191(1), 2014). The frequency, pressure, focal width, shock wave rate, and power density of the lithotripter is selected such that a biofilm is disrupted, while minimizing potential damage to surrounding tissues of the patient. Alternatively, the application of ultrasound energy can be utilized in a focussed manner to exert a biocidal effect to the infectious microorganisms and biofilm colonies. In this way, the method of applying ultrasound energy through a lithotripter aids in the sanitization of an infected implant.

In some embodiments, the frequency of the oscillating acoustic pressure wave is from about 1 kHz to about 60 kHz. In some embodiments, the frequency is about 10 kHz to about 40 kHz. In some embodiments, the frequency is about 1 kHz, about 5 kHz, about 10 kHz, about 15 kHz, about 20 kHz, about 25 kHz, about 30 kHz, about 35 kHz, about 40 kHz, about 45 kHz, about 50 kHz, about 55 kHz, or about 60 kHz.

In some embodiments, the pressure generated by the lithotripter is about 5 MPa to about 160 MPa. In some embodiments, the pressure is about 10 MPa to about 40 MPa. In some embodiments, the pressure is about 1 MPa, about 5 MPa, about 10 MPa, about 15 MPa, about 20 MPa, about 25 MPa, about 30 MPa, about 35 MPa, about 40 MPa, about 50 MPa, about 60 MPa, about 70 MPa, about 80 MPa, about 90 MPa, about 100 MPa, about 120 MPa, about 140 MPa, or about 160 MPa.

In some embodiments, the spatial distribution of acoustic energy or focal width is from about 1 mm to about 30 mm. In some embodiments, the focal width is about 5 mm to about 15 mm. In some embodiments, the focal width about 1 mm, about 5 mm, about 10 mm, about 15 mm, about 20 mm, about 25 mm, or about 30 mm In some embodiments, the shock wave rate is about 10 shock waves per minute to about 200 shock waves per minute. In some embodiments, the shock wave rate is about 20 shock waves per minute to about 80 shock waves per minute. In some embodiments, the shock wave rate is about 10 shock waves per minute, about 20 shock waves per minute, about 30 shock waves per minute, about 35 shock waves per minute, about 40 shock waves per minute, about 45 shock waves per minute, about 50 shock waves per minute, about 55 shock waves per minute, about 60 shock waves per minute, about 80 shock waves per minute, about 100 shock waves per minute, about 120 shock waves per minute, about 140 shock waves per minute, about 160 shock waves per minute, about 180 shock waves per minute, or about 200 shock waves per minute.

In some embodiments, the power density is from about 0.1 W/cm$^2$ to about 25,000 W/cm$^2$. In some embodiments, the power density is from about 1 W/cm$^2$ to about 10,000 W/cm$^2$. In some embodiments, the power density is from about 20 W/cm$^2$ to about 5,000 W/cm$^2$. In some embodiments, the power density is from about 100 W/cm$^2$ to about 3,000 W/cm$^2$.

The ultrasound may be applied prior to performing a needle aspiration biopsy. Any microorganisms present in a biofilm can be loosened to increase the likelihood of detection of the biofilm-forming microorganism. Alternatively, the ultrasound may be applied following a first unsuccessful needle aspiration biopsy to increase the likelihood that any biofilm-forming bacteria are detected. Thus, in some embodiments, ultrasound is applied prior to performing a needle aspiration biopsy. In some other embodiments, ultrasound is applied after a first needle aspiration biopsy is performed.

The inventor has further shown that anthocyanins, anthocyanidins and metabolites thereof, in particular, PCA and 2,4,6 THBA function as broad spectrum antimicrobial agents. These compounds are useful for treating an infection on the surface of an implant or other surface of a patient. These compounds are particularly effective in treating biofilm infections stemming from yeast and bacteria.

As described above, the methods described herein include determining if an infection, including a biofilm infection, is present on or around the surface of the implant or other surface of a patient. The methods described herein further include administering an effective amount of an anthocyanin or an anthocyanidin or metabolites thereof, preferably PCA and 2,4,6 THBA as an anti-microbial agent.

Prior to the invention described herein, there was a need for agents that can treat infected implants. It was discovered by the inventor that anthocyanin and anthocyanidin compounds, in particular, PCA and 2,4,6, THBA are such chemical agents. It has been shown (see FIGS. 6 and 32) that PCA and 2,4,6 THBA have the ability to kill a wide spectrum of microbes. For example, FIG. 6 provides the results of testing showing that PCA, was effective against all bacteria tested in addition to yeast *C. albicans* and highly virulent *K. pneumonia*. PCA was also demonstrated to be effective against difficult infectious microorganisms including *S. aureus* 6538 and 33591 (MRSA) and *P. aeruginosa*.

Figure 32:
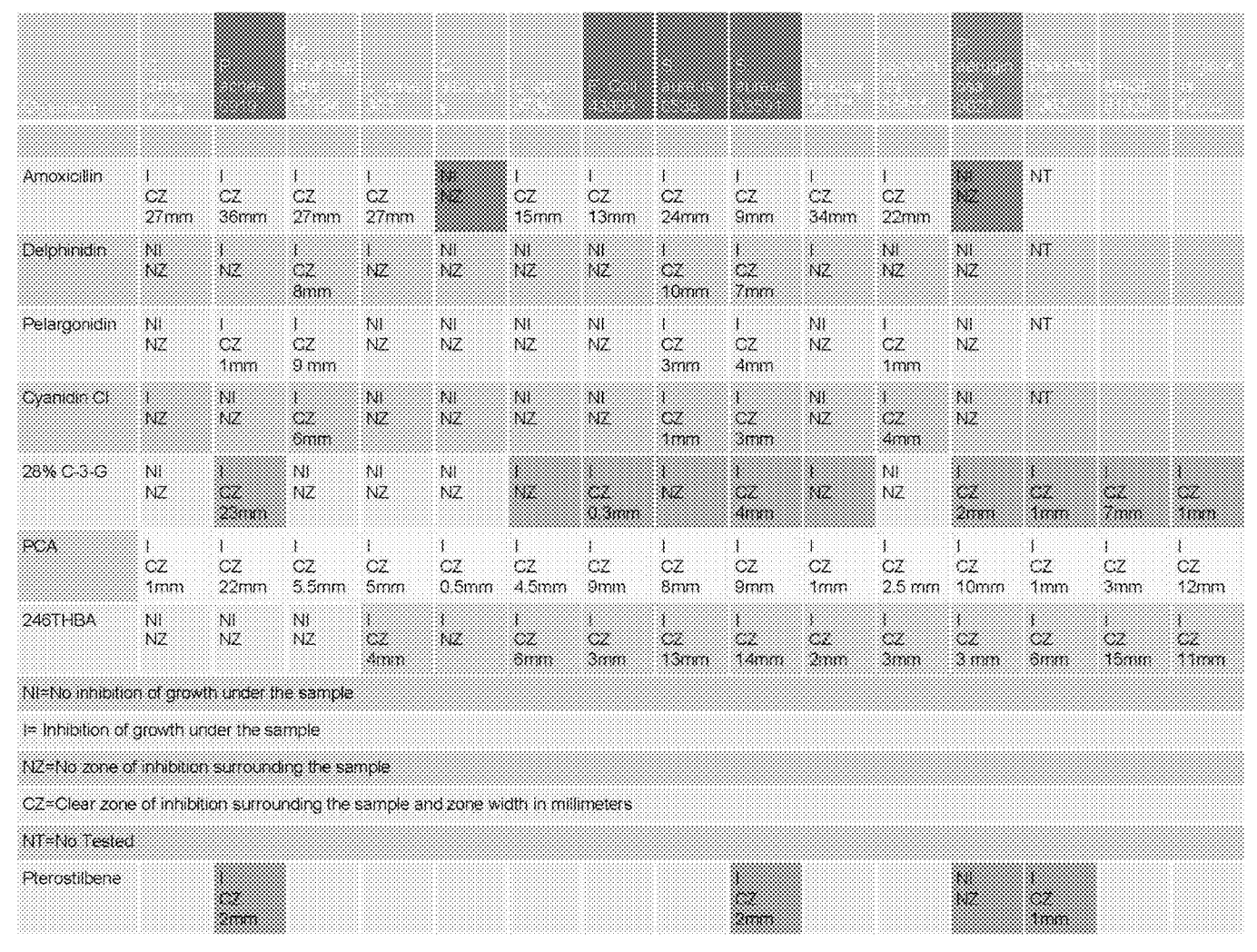

PCA was also effective on *C. albicans*, which is important considering its ability to form biofilms and difficulty in treating *C. albicans* when existing within a catheter or an implant. In FIG. 32, it is shown that PCA is effective against *C. difficile, P. acnes* 6919, *E. coli* 8739 and 43895, *S. Aureus* 6538, *S. Aureus* 33591, *P. Aeruginosa* 9027, methicillin resistant *staphylococcus epidermis* (MRSE), including MRSE ATCC 51625, and *Legionella* 43662, and others. FIG. 32 shows that 2,4,6 THBA is effective against *E. coli* 8739 and 43895, *S. Aureus* 6538, *S. Aureus* 33591, *P. Aeruginosa* 9027, methicillin resistant *staphylococcus epidermis* (MRSE), including MRSE ATCC 51625, and *Legionella* 43662, and others.

Implants, such as total joint implants and dental implants, are often infected with biofilms that are formed from these aforementioned microbes amongst other types of microbes, which can be difficult to treat. Biofilms are comprised of bacteria that form colonies and produce a surrounding matrix film to protect themselves. The biofilm forming bacteria can form colonies that attach to foreign bodies, each other and tissues. The bacteria aggregate in clusters and are surrounded by extracellular polymer matrix. The biofilms are hard to destroy and therefore kill the underlying bacteria and provide the basis for much of the antibiotic resistance that has developed. The formation of a biofilm is a two-step process: 1. adherence of cells to a foreign body surface; and 2. accumulation of cells to form multilayered cell clusters.

The inventor has shown that PCA was able to stop the formation of a biofilm as well as kill bacterial in already formed biofilms. The biofilms tested were *Pseudomonas Aeruginosa* ATCC 700888 and *Staphylococcus aureus* ATCC 33591 (MRSA). The tests are described in more details in Examples 7 and 8 and FIGS. 35 and 36.

Thus, in some embodiments, following the determination that an implant or other surface of a patient is infected, the implant or other surface of a patient is treated with an effective amount of an anthocyanin or anthocyanidin or a metabolite thereof in situ. Exemplary and non-limiting anthocyanins include cyanidin-3-glucoside or delphinidin-3-glucoside, cyanidin-3-galactoside, and pelargonidin-3-galactoside. Exemplary and non-limiting anthocyanidins include cyanidin, delphinidin, pelargonidin, malvidin and petunidin. In particular, the implant or other surface of a patient is treated with a metabolite of anthocyanins and anthocyanidins including PCA, 2,4,6 THBA, and combinations thereof. The anthocyanin or anthocyanidin or metabolite thereof, including PCA or 2,4,6 THBA, may be administered as pure crystals or as part of a composition described herein.

In some embodiments, are methods of prophylactically treating a preoperative skin incision site, comprising administering an anthocyanin, an anthocyanidin or a metabolite thereof to a patient in need of such treatment an effective amount of the anthocyanin or anthocyanidin compound wherein microbial growth is prevented or reduced prior to any surgery involving the installation of an implant.

In some embodiments, a method of disinfecting a surface of an implant or other surface of a patient includes contacting said surface with an anthocyanin, an anthocyanidin and/or a metabolite thereof in an effective amount of the anthocyanin, anthocyanidin and/or metabolite compound wherein microbial growth is prevented, reduced or eliminated. In some embodiments, the microbial growth that is reduced includes infections and biofilm infections on the surface of an implant or other surface of a patient that may be an endogenous or exogenous source, including but not limited to MRSA, *P. acnes, S. aureus, P. aeruginosa, E. coli, S. epidermidis, S. pneumonia, Streptococcus* species, *C. difficile* and *Legionella*.

In some embodiments, the effective amount of the anthocyanin or anthocyanidin or metabolite thereof, including PCA or 2,4,6 THBA or a combination thereof is from about 1 μg to about 1000 mg. In some embodiments, the effective amount is from about 1 μg to about 500 mg. In some embodiments, the effective amount is from about 1 μg to about 50 mg. In some embodiments, the effective amount is from about 1 μg to about 10 mg. In some embodiments, the effective amount is from about 1 μg to about 1000 μg. In some embodiments, the effective amount is from about 1 μg to about 500 μg. In some embodiments, the effective amount is from about 1 μg to about 50 μg.

In some embodiments, the anthocyanin, anthocyanidin, or metabolite thereof is incorporated as pure crystals in an implantable material, such as a mesh including titanium or stainless steel. The crystals are applied to the metal where there is surface configuration that provides for housing of the crystal on the surface. In this way, the crystals remain in place in crystal form until activated when subject to fluid common to the mammalian body. The anthocyanin, anthocyanidin, or metabolite thereof can be present as a polymorphous, semi-crystalline, hydrate, amorphous or polyamorphous forms.

The crystals of the anthocyanin or anthocyanidin or metabolite thereof may be micronized using known micronization techniques known in the art. The micronized crystals may be useful for embedding upon a surface of to enhance the dissolution of the compound when provided in a solution or when administered in vivo to a patient. Thus, in some embodiments, the crystals have a mean particle distribution of <1000 μm, <500 μm, <400 μm, <300 μm, <200 μm, <100 μm, <50 μm, or even <10 μm. The particles may have a "d90", "d50", and "d10" distribution of the forgoing sizes, meaning that (90%, 50%, or 10%, respectively) of particle sizes are less than a specified size or size range. For example, as specified, d90≤90 μm means that 90% of the particle sizes within a distribution of particles are less than or equal to 90 μm.

In some embodiments, the anthocyanin, anthocyanidin, or metabolite thereof is substantially pure. In some embodiments, the compounds are at least 75% to greater than 99% pure. In some embodiments, the compounds are at least 90%, 95%, 99%, or 99.99% pure as assessed by techniques routine in the art, such as high performance liquid chromatography (HPLC).

In some embodiments, the anthocyanin, anthocyanidin, or metabolite thereof is provided as a pharmaceutically acceptable salt form. Pharmaceutically acceptable salts forms are those formed by, for example, contacting a free base of the compound with a suitable acid in a suitable solvent under suitable conditions that will form an acid addition salt. The salt form includes alkali metal salts such as, for example, sodium or potassium salts, alkaline earth metal salts such as, for example, calcium and magnesium salts, and salts with organic or inorganic acid such as, for example, hydrochloric acid, hydrobromic acid, nitric acid, sulfuric acid, phosphoric acid, citric acid, formic acid, maleic acid, succinic acid, tartaric acid, methanesulphonic acid, toluenesulphonic acid etc.

The anthocyanin, anthocyanidin or metabolite thereof may be administered to treat the infected implant or other surface of a patient by methods commonly used in the art for the treatment of infected implants with antimicrobial compounds. These include, but are not limited to, topical administration above the area of infection, transdermal administration above the area of infection, enteric administration (e.g., oral or rectal), sublingual administration, or other parenteral injection, including epidermal injection, intravenous injection, subcutaneous injection, intra muscular injection, intra-articular injection, or other injection to administer the anthocyanin or anthocyanidin in proximity to the infected implant or other infected surface of a patient.

In some embodiments, the anthocyanin, anthocyanidin, or metabolite thereof is administered to a patient having an infected implant or other surface of a patient at least one time. In some embodiments, once a positive diagnosis of infection of an implant or other surface of a patient is established, the anthocyanin, anthocyanidin, or metabolite thereof is administered at a set frequency. The frequency of administration may be once a week, twice a week, three times a week, four times a week, five times a week, six times a week, daily, twice daily, three times daily, four times daily, or hourly. Alternatively, the anthocyanin, anthocyanidin, or metabolite thereof may be administered continuously through infusion or irrigation of the infected surface of a patient or implant. This type of administration is possible because the anthocyanin or anthocyanidin or metabolites thereof described herein are safe and with little to no demonstrated local or systemic toxicity.

Alternatively, in some other embodiments, the anthocyanin, anthocyanidin, or metabolite thereof is administered prophylactically to a patient receiving an implant to prevent or reduce the likelihood of an infection. In some embodiments, the patient is also prophylactically monitored using the diagnostic methods described herein to identify an infection prior to a clinical manifestation of the infection.

In some embodiments, the anthocyanin, anthocyanidin, or metabolite thereof is administered with a second pharmaceutical agent. Suitable and non-limiting second pharmaceutical agents include additional anthocyanin or anthocyanidin compounds or metabolites thereof, antibiotics, analgesics, and anti-inflammatory agents.

The therapeutic effective dose may vary depending on a wide variety of factors. For instance, the dose may vary depending on the formulation, method of application of the therapeutic reagent or combination with other reagents, or compositions, compounds or combination of compositions or compounds to the infected implant or surface of a patient.

Compositions

Disclosed herein are antimicrobial compositions for treating infected implants or other infected surfaces of a patient. The disclosed antimicrobial reagents and compositions can be used to eliminate, reduce, and/or prevent microorganism growth, viability, or survival. In particular, the compositions including an anthocyanin or anthocyanidin or metabolite thereof in an effective amount to eliminate, reduce, and/or prevent microorganism growth, viability, or survival of a biofilm causing an infection of an implant or other surface of a patient.

The present disclosure provides for pharmaceutical compositions whereby the anthocyanin, anthocyanidin, anthocyanin metabolite, anthocyanidin metabolite, anthocyanin metabolite, or metabolites thereof, are isolated reagents. Preferably the present composition includes PCA, 2,4,6 THBA or a combination thereof.

In some embodiments, the present invention provides for a pharmaceutical composition for treating an infected implant or other surface of a patient including: a) an anthocyanin; b) anthocyanidin; c) a metabolite of an anthocyanin or anthocyanidin such as C3G, PCA, 2,4,6 THBA, vanillic and hippuric acid. Preferably the present composition includes PCA, 2,4,6 THBA, or a combination thereof.

Suitable and non-limiting compositions include those that can be applied to or near the site of the infected implant or infected surface of a patient. The composition comprising anthocyanin or anthocyanidin or metabolite thereof may be in the form of a liquid solution, suspension, a dispersion, or an emulsion.

In some embodiments, the anthocyanin, anthocyanidin, or metabolite thereof is about 0.5% to about 90% by weight of the composition. In some embodiments, the anthocyanin, anthocyanidin, or metabolite thereof is about 0.5% to about 70% by weight of the composition. In some embodiments, the anthocyanin, anthocyanidin, or metabolite thereof is about 0.5% to about 50% by weight of the composition. In some embodiments, the anthocyanin, anthocyanidin, or metabolite thereof is about 0.5% to about 30% by weight of the composition. In some embodiments, the anthocyanin, anthocyanidin, or metabolite thereof is about 0.5% to about 20% by weight of the composition. In some embodiments, the anthocyanin, anthocyanidin, or metabolite thereof is about 5% to about 30% by weight of the composition. In some embodiments, the anthocyanin, anthocyanidin, or metabolite thereof is about 0.5% to about 20% by weight of the composition. In some embodiments, the anthocyanin or anthocyanidin or metabolite thereof is about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, or about 90% by weight of the composition.

In some embodiments, the anthocyanins or anthocyanidins and metabolites thereof is provided in concentrations of about 10 to 200 mM. In other embodiments, anthocyanins, or anthocyanidins, or metabolites thereof are provided in any recited composition or method of use in a range of between 20 to 200 mM. In yet other embodiments, the anthocyanin, anthocyanidin, or metabolites thereof provided in any recited composition or method of use is provided in a range of between 20 to 100 mM. In yet other embodiments, the anthocyanin, anthocyanidin, or metabolites thereof provided in any recited composition or method of use is provided in a range of between 50 to 100 mM. In yet other embodiments, the anthocyanin, anthocyanidin, or metabolites thereof provided in any recited composition or method of use is provided in a range of between 20 to 50 mM.

In some embodiments, the anthocyanin, anthocyanidin, or metabolite thereof is in the form of crystals that are embedded into a composition. Exemplary and non-limiting compositions in which the crystals are embedded include a cloth or a mesh, such as titanium or stainless steel. In some embodiments, the anthocyanin, anthocyanidin, or metabolite thereof is in the form of a powder. A powder form is contemplated for further use in a composition described herein (e.g., to be dissolved or suspended therein) or imbedded into a composition.

In some embodiments, the disclosed composition can be selected from anthocyanins, anthocyanidins, metabolites of anthocyanin and anthocyanidin compounds, or a combination thereof. By way of example, the anthocyanin can be selected from cyanidin-3-glucoside or delphinidin-3-glucoside, cyanidin-3-galactoside, and pelargonidin-3-galactoside and combinations thereof. Also by way of example, the anthocyanidins can be selected from cyanidin, delphinidin, pelargonidin, malvidin, petunidin, and combinations thereof. In particular, metabolites of anthocyanins and anthocyanidins can be selected from PCA and 2,4,6 THBA and combinations thereof.

In some embodiments, the anthocyanin, anthocyanidin, or metabolite thereof is in a solution. In some embodiments, the metabolite of the anthocyanin or anthocyanidin is PCA or 2,4,6 THBA. In some embodiments, the metabolite of the anthocyanin or anthocyanidin is PCA. In some embodiments, the metabolite of the anthocyanin or anthocyanidin is 2,4,6 THBA.

In some embodiments, the anthocyanin, anthocyanidin, or a mixture or combination thereof is provided in a composition including a carrier that includes 50% to 91% isopropyl alcohol. In some embodiments, PCA, 2,4,6 THBA, or a mixture or combination thereof is provided in a composition including a carrier that includes 50% to 91% isopropyl alcohol. In some embodiments, PCA is provided in a composition including a carrier that includes 50% to 91% isopropyl alcohol. In some embodiments, 2,4,6 THBA is provided in a composition including a carrier that includes 50% to 91% isopropyl alcohol.

The compositions described herein are suitable for routes of administration including oral, injection, intravenous, subcutaneous, epidermal, topical, sublingual, buccal, inhalation, intradermal, subcutaneous, intra articular, soft tissue, and cutaneous.

Oral administration of the compositions of this disclosure, including oral gavage, may include a liquid or semisolid form, tablet, pill, capsule, powder, or gel. Preferably, oral administration will be in a liquid composition. Compositions including a liquid pharmaceutically inert carrier such as water may be considered for oral administration. Other pharmaceutically compatible liquids or semisolids may also be used. The use of such liquids and semisolids and manufacturing of tablet, pill, powder, or gel compositions is well known to those of skill in the art. The injectable compositions be in liquid or semi-liquid form. Other pharmaceutically compatible liquids or semi-liquids may also be used. The use of such liquids and semi-liquids is well known to those of skill in the art.

In some embodiments, the composition is formulated as a topical composition. More preferable, the vehicle of the topical composition delivery is in the form of a liquid, salve, soap, spray, foam, cream, emollient, gel, ointment, balm or transdermal patch.

In some embodiments, the compositions can be in the form of an aqueous solution. In some embodiments, the compositions disclosed herein are in the form of a liquid, gel, suspension, dispersion, solid, emulsion, aerosol, for example, powders, tablets, capsules, pills, liquids, suspensions, dispersions or emulsions. In addition, the compositions disclosed herein can be in the form suitable for dilutions. Similarly, the compositions can be in the form of a powder, cream, paste, gel or solid that can be reconstituted.

Other components can be present in the composition, if desired. For example, the antimicrobial composition can also include at least one additive selected independently from a carrier, a diluent, an adjuvant, a solubilizing agent, a suspending agent, a filler, a surfactant, a secondary antimicrobial agent, a preservative, a viscosity modifier, a thixotropy modifier, a wetting agent, an emulsifier, or any combinations thereof. For example, the disclosed antimicrobial composition can further comprise at least one surfactant selected from a cationic surfactant, an anionic surfactant, a non-ionic surfactant, and an amphoteric surfactant. Additionally, the disclosed antimicrobial and/or pharmaceutical compositions may further comprise medicament is selected from the group consisting of anesthetic agents, cleansers, antiseptic agents, scar reducing agents, immunostimulating agents, antiviral agents, antikeratolytic agents, anti-inflammatory agents, antifungal agents, antihistamine agents, antibacterial agents, bioadhesive agents, inhibitors of prostaglandin synthesis, antioxidants, and mixtures thereof.

Also, the disclosed antimicrobial compositions can optionally include one or more additives such as carriers, adjuvants, solubilizing agents, suspending agents, diluents, surfactants, other antimicrobial agents, preservatives, fillers, wetting agents, antifoaming agents, emulsifiers, and additives designed to affect the viscosity or ability of the composition to adhere to and/or aid in the treatment of an infected implant or other surface of a patient.

The disclosed antimicrobial compositions, including the selected active components, including the anthocyanins or anthocyanidins and metabolites thereof, are without causing significant undesirable biological effects or interacting in a deleterious manner with any of the other components of the composition in which it is contained.

In other examples, the antimicrobial compositions disclosed herein can further comprise a carrier. The term "carrier" means a compound, composition, substance, or structure that, when in combination with a compound or composition disclosed herein, facilitates preparation, administration, delivery, effectiveness, or any other feature of the compound or composition. Examples of carriers include water, isopropyl alcohol ethanol, polyols (propyleneglycol, polyethyleneglycol, glycerol, and the like), polyoxyalkylenes, e.g., poly(oxyethylene)-poly(oxypropylene) polymers, benzyl alcohol or butanediol, vegetable oils, and suitable mixtures thereof. "Pharmaceutically acceptable carrier" means a compound, composition, substance, or structure that is useful in neither preparing a pharmaceutical composition which is generally safe, non-toxic, and neither biologically nor otherwise undesirable and includes that which is acceptable for veterinary as well as human pharmaceutical use. In addition, the carrier maybe aqueous or oily. The carrier may further include suitable pH modifying agents including alkali metal salts, such as sodium or potassium hydroxide, or acidic compounds, such as hydrochloric acid or other weaker organic carboxylic acids. In addition, further oxidation stabilizers, e.g., sodium bisulfite or preservatives, e.g., benzyl alcohol, may advantageously be incorporated into the compositions.

In a further example, the antimicrobial compositions disclosed herein can also comprise adjuvants such as preserving, wetting, emulsifying, suspending agents, and dispensing agents. Prevention of the action of other microorganisms can be accomplished by various antifungal agents, for example, parabens, chlorobutanol, phenol, and the like.

Suitable suspending agents can include, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

The disclosed antimicrobial compositions can also comprise solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl 1 alcohol, polyethyleneglycols and fatty acid esters of sorbitan or mixtures of these substances, and the like. The additives can be present in the disclosed compositions in any amount for the individual anthocyanin, anthocyanidin or metabolite thereof compound components.

The composition may further be in the form of a gel or include an in situ gel-forming agent that results in the release of the anthocyanin, anthocyanidin or metabolite thereof over an extended period. Such extended release gel-forming compositions are generally known in the art (see e.g., WO 1995/035093 and US 20030157178A1).

Some embodiments are kits for diagnosing and treating an infected implant or surface of a patient with a therapeutically effective amount of an anthocyanin or anthocyanidin or metabolite thereof. The kit may include a minimally invasive sampling device for detecting the presence of an infectious or pathological microorganism, such as a sterile wrapped needle and syringe.

The kit further includes an anthocyanin, anthocyanidin or metabolite thereof in an amount effective for the treatment of an infected implant or surface of a patient. The anthocyanin, anthocyanidin, or metabolite thereof can be provided in a liquid or gellable composition described herein. Alternatively, the anthocyanin, anthocyanidin, or metabolite thereof can be provided as a crystal present in a vial that can be further prepared as a liquid composition or embedded in an implantable material. The amount of the anthocyanin, anthocyanidin, or metabolite thereof present in the kit may range from 1 mg to greater than or equal to 10,000 mg. The kit may also include culturing devices including culture plates, tubes, and growth media as known in the art. The kit may further include instructions for diagnosing and treating a patient suspected of having an infection of an implant or other surface according to the invention.

It will be readily apparent to one of ordinary skill in the relevant arts that suitable modifications and adaptations to the compositions, methods, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any and all variations or iterations. The scope of the compositions, formulations, methods, and processes described herein include all actual or potential combinations of embodiments, aspects, options, examples, and preferences herein described. Non-limiting examples of the inventive embodiments of the invention are described in the examples below.

EXAMPLES

Example 1: Use of In Vitro Studies for Antimicrobial Susceptibility Testing of Anthocyanins, Anthocyanidins, or Metabolites and Compounds Thereof This example describes the method for testing the antimicrobial susceptibility of anthocyanins, anthocyanidins, or metabolites and compounds thereof. The Kirby-Bauer method of disc diffusion was used for testing, following a standard set of procedures recommended by the NCCLS. In this methodology, a set of discs saturated with either testing compounds or a control was placed on inoculated agar plates. The plates were inoculated with organisms listed in the tables provided in FIG. 6, including *C. difficile, P. acnes, C. perfringens, L. casei, C. albicans, E. coli*, ATTC 8739 and ATCC 43895, *S. aureus, S. mutans, S. pyogenes, P. aeruginosa* and *K. pneumonia*. The control sample was amoxicillin, an antimicrobial with very effective broad-spectrum antibiotic properties. Samples included delphinidin, pelargonidin, cyanidin CI, 28% cyanindin-3-glucoside (C3G), protocatechuic acid (PCA) and 2,4,6 Trihydroxybenzaldehyde (2,4,6 THBA).

After 18, 24, or 48 hours of incubation, depending upon the microorganism, each plate was examined. The diameters of the zones of complete inhibition were measured, including the diameter of the disc. Zones were measured to the nearest millimeter, using sliding calipers. The size of the zones of inhibition was interpreted by referring to NCCLS standard. Results were interpreted as follows: NI was no inhibition of growth under the test sample, I was inhibition of growth under the test sample, NZ indicated no zone of inhibition surrounding the test sample, and CZ indicated a clear zone of inhibition surrounding the sample and zone width in millimeters. See FIG. 6 for complete results.

Results

Referring to FIG. 6 and FIG. 32, the testing samples had bactericidal and bacteriostatic activity against many of the organisms. Of note, *P. acnes*, an organism that is very difficult to treat, often requiring multiple current antibiotics for effective treatment, was susceptible to both C3G and PCA. Indeed, both of these test samples were bactericidal against *P. acnes*. Additionally, PCA was also effective against *Staphylococcus aureus* ATCC 33591, known as Methicillin Resistant *Staph Aureus* (MRSA), *Staphylococcus epidermidis* ATCC 51625, known as Methicillin Resistant *Staph Epidermidis* (MRSE), *E. coli* 8739 and 43895, and *Legionella* 43662.

PCA was also shown to have some effectiveness against *Pseudomonas aeruginosa*, a common pathogen in wounds, especially burns, as well as chronic lung infections. Amoxicillin, the control sample, had no effect on *P. aeruginosa*. Similarly, *Candida albicans*, frequently a co pathogen in wounds, was susceptible to PCA.

PCA was also shown to have some effectiveness against *Pseudomonas aeruginosa*, a common pathogen in wounds, especially burns. Amoxicillin, the control sample, had no effect on *P. aeruginosa*. Similarly, *Candida albicans*, frequently a co pathogen in wounds, was susceptible to PCA.

In summary, the present invention provides advantages over the prior art, including providing anthocyanin, anthocyanidin, their metabolites or combinations thereof to a wound to provide a reduction or elimination of bacteria. It is contemplated that the invention will also find use in the treatment of surfaces, including medical devices and medical implants, to reduce or eliminate bacteria.

Example 2: Use of Mouse Model to Determine Dose Levels and Intervals of Test Samples Methods:

Mice had back skin tape stripped and the stripped site (wound) was infected with *P. aeruginosa* (ACTA 9027). The test reagents were applied topically in an aqueous solution on the stripped site at two hours and daily for four days.

Cyanidin 3-glucoside (C3G), an anthocyanin, and its main metabolite PCA were formulated and tested at several doses. The aqueous carrier was water. The C3G formulation included 50 mM, 100 mM and 200 mM dose concentrations. Similarly, the PCA formulation included at 50, 100 and 200 mM dose concentrations.

Results

Figure 9A:
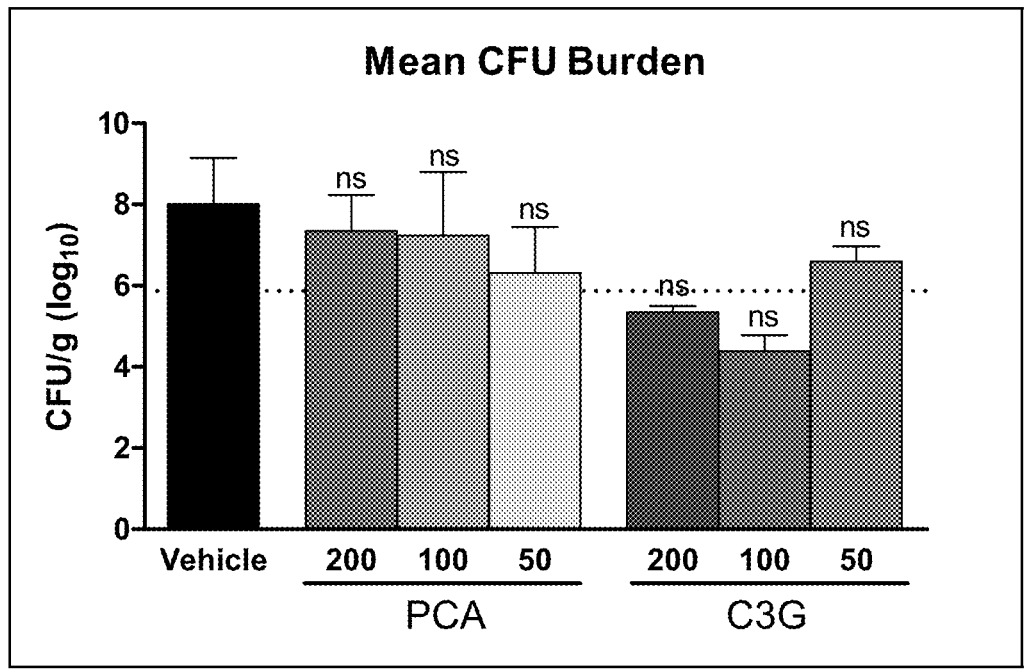
FIG. 9A shows the results of a rodent back skin tape study where concentrations of PCA and C3G in a vehicle of water were utilized to determine effectiveness against *P. aeruginosa* skin infections.

Results were collected from the mice at day five. Both C3G and PCA decreased the bacterial burden; however, none were statistically significant. See FIG. 9A. There was a trend towards a decreasing concentration of PCA, with 50 mM being the most effective. The most effective dose of C3G was 100 mM. It is contemplated that because C3G degrades to PCA in this environment, the test results may indicate that C3G was not being tested alone, but rather was a combination of C3G and its metabolites, including a combination of C3G and PCA as the effective agents.

Example 3: Use of Mouse Model to Further Determine Effective Dose Levels and Dose Intervals of Test Samples Methods:

Mice had back skin tape stripped and the stripped site (wound) was infected with *P. aeruginosa* (ACTA 27853). The test reagents were applied topically in an aqueous solution on the stripped site at two hours and daily on day 1, 2 and 3.

C3G, an anthocyanin and its main metabolite PCA were formulated and tested at several doses. The aqueous carrier was water. The C3G formulation included 100 mM and 200 mM dose concentrations and the PCA formulation included 25 and 50 mM dose concentrations.

Results

Figure 9B:
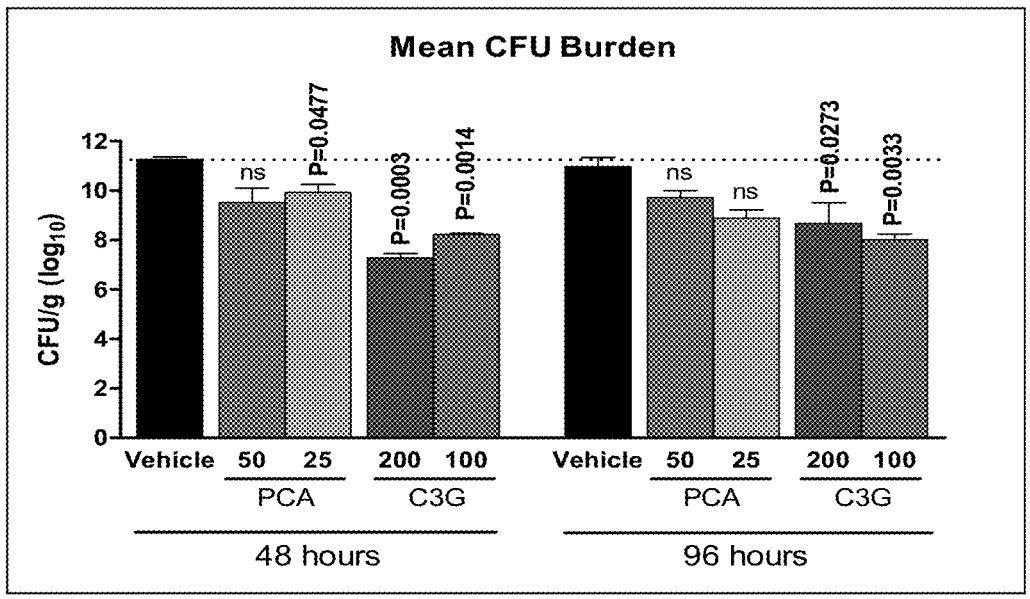
FIG. 9B shows the results of rodent back skin tape study where concentrations of PCA and C3G in a vehicle of water were utilized to determine effectiveness against *P. aeruginosa* skin infections.

Results were collected from the mice at day two and four. Both C3G and PCA decreased the bacterial burden at 48 and 96 hours. (See FIG. 9B). The most significant decrease of bacteria was observed at 25 mM of and 100 and 200 mM of C3G. Although PCA at 25 mM reduced the bacterial burden at both time periods, its activity was statistically significant at 48 hours. C3G at both 100 mM and 200 mM significantly reduced the bacterial burden at 48 and 96 hours.

Example 4: Use of a Mouse Model for Wound Healing

Methods:

Mice were shaved but unstrapped and uninfected (normal rodent skin). The test reagents were applied topically in an aqueous solution on the unstripped site at two hours and daily on day 1, 2 and 3.

Testing reagents consisted of C3G and PCA formulated at one dose, 100 µM in an aqueous solution.

Figure 10A:
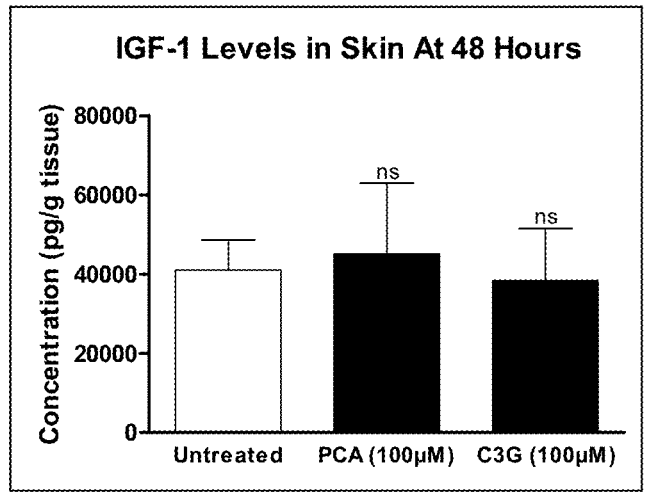
FIG. 10A shows the results of an additional rodent back skin tape study to determine effective dosages of PCA and C3G in a vehicle of water that would be bactericidal for *P. aeruginosa*.
Figure 10B:
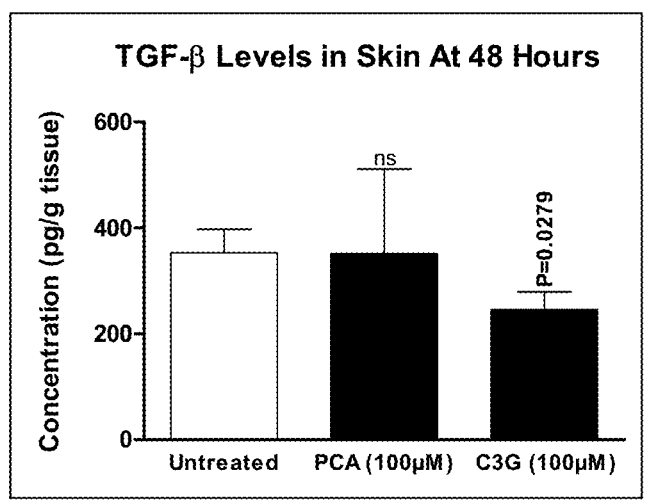
FIG. 10B shows the results of an additional rodent back skin tape study to determine effective dosages of PCA and C3G in a vehicle of water that would be bactericidal for *P. aeruginosa*.
Figure 10C:
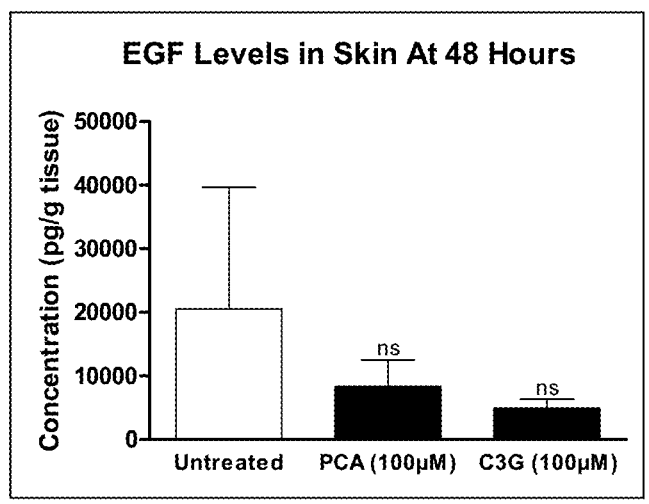
FIG. 10C shows the results of an additional rodent back skin tape study to determine effective dosages of PCA and C3G in a vehicle of water that would be bactericidal for *P. aeruginosa*.

Results:

Referring to FIG. 10, there was little or no stimulation of IGF-1 and TGF-β at local levels observed at the 100 µM concentration of testing reagents. In fact, levels of EGF actually decreased below normal levels. There was observed a decrease of all three local growth hormones at 100 uM of C3G. These results suggest that mice skin differs in response to a dose that has been shown to stimulate human synovium to produce IGF-1. Thus, this low of a dose is not useful for rodents for this purpose.

Example 5: Use of Mouse Model to Determine Isolated Effect of 25 mM Solution of PCA in Various Environments Methods:

Four different conditions were used: mice had back skin tape stripped and the stripped site (wound) was infected with *P. aeruginosa*; mice had back skin stripped and were not infected, mice had taped stripped, infected and treated with PCA, mice were tape stripped, uninfected, and treated with PCA. When used, the PCA test reagent was applied topically in an aqueous solution on the stripped site at two hours and 24 hours.

The testing reagents consisted of and PCA formulated at one dose, 25 mM, in an aqueous solution. Levels of IGF-1, TGF-β, and EGF levels in the skin tissue at 48 hours were measured by ELISA. There were two control groups; the stripped skin and the stripped skin and infected.

Figure 13A:
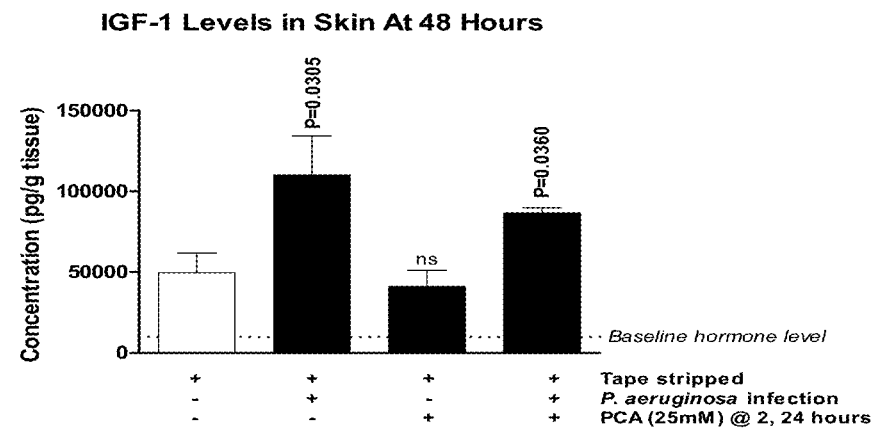
FIG. 13A shows the IGF-1 response to 25 mM PCA in various environments, including tape stripped, tape stripped and infected with *P. aeruginosa*, tape stripped and treated with PCA, and tape stripped infected with *P. aeruginosa*, and PCA treated.
Figure 13B:
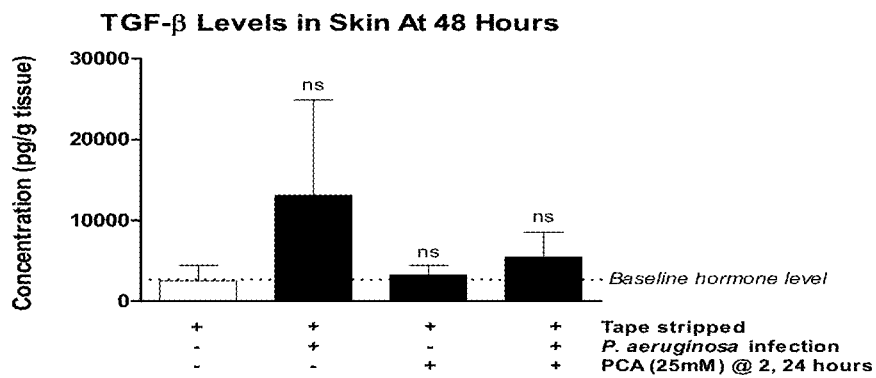
FIG. 13B shows the TGF-β response to 25 mM PCA in various environments, including tape stripped, tape stripped and infected with *P. aeruginosa*, tape stripped and treated with PCA, and tape stripped infected with *P. aeruginosa*, and PCA treated.
Figure 13C:
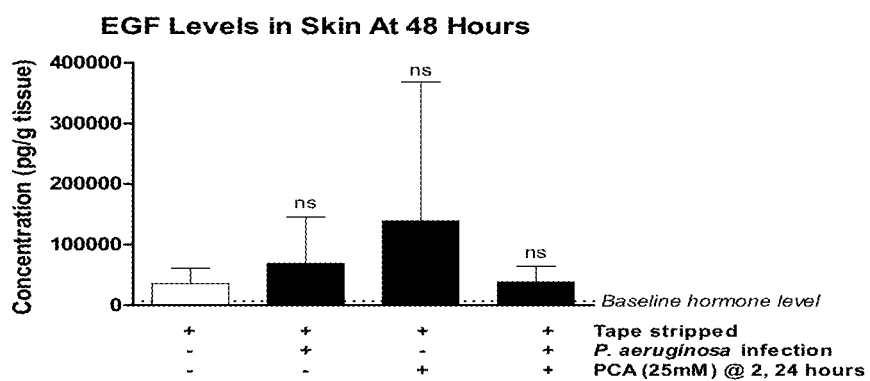
FIG. 13C shows the EGF response to 25 mM PCA in various environments, including tape stripped, tape stripped and infected with *P. aeruginosa*, tape stripped and treated with PCA, and tape stripped infected with *P. aeruginosa*, and PCA treated.

Results:

Referring to FIG. 13, the infected stripped skin showed the highest level with IGF-1 (statistically significant) and TGF-β. This is representative of tissue response to injury and infection; similarly, the EGF response was very inconsistent compared to the other two growth hormones.

The EGF response levels were different than either IGF-1 or TGF-β. They were highest in the stripped and uninfected wound and lowest in the stripped, infected and treated wound. Therefore, the treatment optimized the amount of hormone production compared to the untreated infection. This is beneficial to limit scarring while promoting healing over the controls. Overall, PCA at 25 mM acts on stripped and infected mice skin and optimizes the IGF-1 production and optimizes the local growth hormones.

Example 6: Use of Mice to Establish Wound Promoting Effect of Compositions

Method:

Fifteen rodents were used to establish the histological findings of stripped skin, stripped and infected skin, and stripped, infected and treated wound. There were two control groups and four experimental groups according to the following:

Control Group 1: three mice with only tape stripped wounds on the back. These mice were not infected or treated. The skin was harvested at time zero, 2 and 48 hours for histology examination.

Control Group 2: three had tape stripped wounds and infection. Tissue submitted at 2 and 48 hours for histological examination.

Experimental Groups: There were 4 experimental groups. In these groups, mice had skin stripped wounds and infection. Treatment varied by reagent and dosage. Testing reagents included PCA at 25 at 25 and 50 mM and C3G at 100 and 200 mM.

*Pseudomonas aeruginosa* (ATCC 27853) procured from American Type Culture Collection, Manassas, Va. was used to infect the experimental groups of mice. The organism was grown overnight at 37° C. at ambient atmosphere trypticase soy agar plates supplemented with 5% sheep blood cells. The culture will be aseptically swabbed and transferred to tubes of trypticase soy broth. The optical density will be determined at 600 nm. The cultures will be diluted to provide an inoculum of approximately 9.0 $\log_{10}$ CFU per mouse in a volume of 100 µL. Inoculum count was estimated before inoculation by optical density and confirmed after inoculation by dilution and back count.

The testing reagents were topically applied at 2 and 24 hours with 100 uL of fluid spread over the wound.

The following histological assessments were conducted:

Surface Cellularity: The histological assessment included the presence or absence of the surface cellularity and the depth of the cells.

Dermis: vascularity and inflammation.

Thickness: The thickness of the dermal layer was observed.

Hair Follicles: The hair follicles and the layer of surrounding cells were observed. Hair follicles presence is critically important to skin wound healing. (Gharzi A, Reynolds A J, Jahoda C A. Plasticity of hair follicle dermal cells in wound healing and induction. Exp Dermatol. 2003 April; 12 (2):126-36). The dermal sheath surrounding the hair follicle has the progenitor cells for contributing fibroblasts for wound healing. (Johada C A, Reynolds A J. Hair follicle dermal sheath cells: unsung participants in wound healing. Lancet. 2001 Oct. 27; 358(9291):1445-8).

Vascularity: Vascularity was observed, but an assessment of angiogenesis was not performed on the 48 hour material since new vascularity takes three to twelve days to develop. (Busuioc C J, et al. Phases of cutaneous angiogenesis process in experimental third-degree skin burns: histological and immunohistochemical study. Rom J Morphol Embryol. 2013; 54(1):163-710.)

Inflammation: The presence of cellular infiltration was observed and its location.

Skin Thickness: The thickness of the skin was estimated related to the uninfected, untreated wound. This depth was estimated on the uniform histology photomicrographs from the surface to the muscle layer.

Results:

The following results were observed in each group:

Control Group 1: Uninfected and Untreated.

Time Zero: (See FIGS. 14-15) At time zero following the wound stripping there was cellular covering of the surface. The dermal layer was not thickened. The hair follicles have a single cellular lining. There was minimal vascularity and no inflammation. The depth of the tissue was considered zero for future bench mark. 0+

2 hours: (See FIGS. 16-17) At 2 hours following the wound stripping the surface remained covered with cellularity. The dermal layer was minimally thickened. The follicles and cellular lining was the same. There was minimal increase in vascularity and inflammation. The increase in the depth of the tissue was considered 0.5+.

48 hours: (See FIGS. 18-19) At 48 hours the wound stripped, uninfected, untreated specimens showed natural history response of surface cellular proliferation and thickness. The dermal layer was thickened. The hair follicles were present with single layer cellular lining. The vascularity was increased in amount compared to the 2 hour specimens. The inflammation was present throughout the dermis and muscle layer. The thickness was considered 0.5+.

Control Group 2: Infected and Untreated.

2 hours: (See FIGS. 20-21) The histological assessment showed the wound stripped, infected, but untreated controls at 2 hours to have multiple cellular covering on surface. There was minimal thickening of the dermal layer. The hair follicles were abundant and had double layer cellular lining. There was minimal vascularity and no inflammation in the specimens. The thickness was assigned 0.5+.

Figure 22:
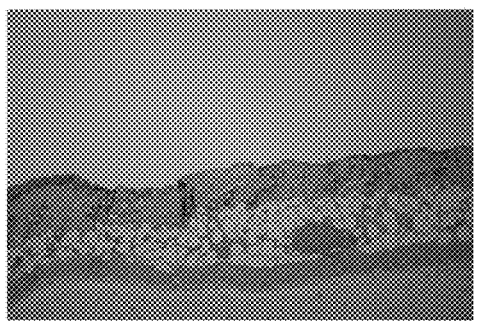
FIG. 22 is a photographic image of a cross section of rodent skin.
Figure 23:
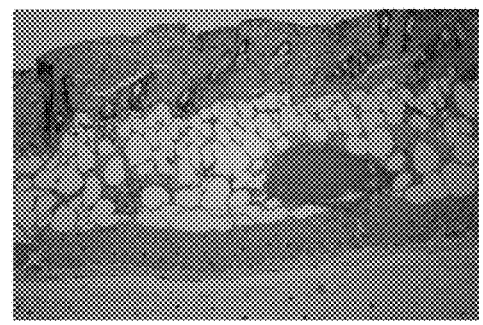
FIG. 23 is a photographic image of a cross section of rodent skin.

48 hours: (See FIGS. 22-23) At 48 hours the surface cellular covering was gone. The dermal layer had minimal thickening. The hair follicles were present, with minimal cellularity lining. There was marked increase in vascularity and minimal inflammation in dermis layer. The depth was considered 0.5+ compared to time zero.

Figure 24:
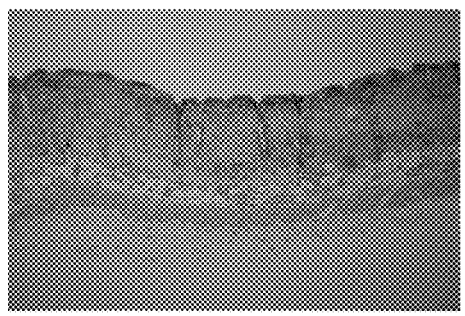
FIG. 24 is a photographic image of a cross section of rodent skin.
Figure 25:
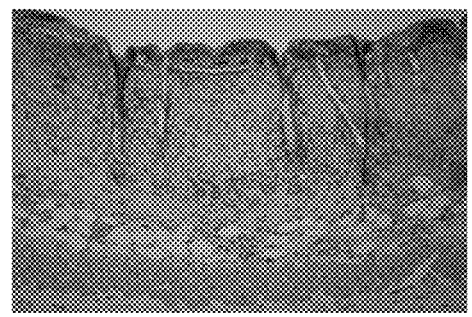
FIG. 25 is a photographic image of a cross section of rodent skin.

Experimental Group PCA 25 mM 48 hours: (See FIGS. 24-25) The cellular covering of the surface was abundant and multiple cell layers. The dermal layer was thickened. The hair follicles were prominent with multiple cellular lining. There was collagen proliferation between the epidermis and dermis. Additionally, there was moderate vascularity, but less than that seen in infected untreated group. There was abundant inflammation and it was greater than was seen in the PCA 50 dose. Thickness was assigned 2+.

Figure 26:
FIG. 26 is a photographic image of a cross section of rodent skin.
Figure 27:
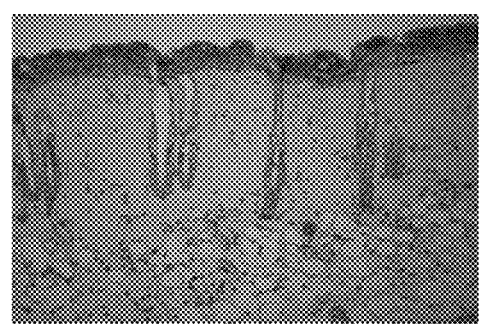
FIG. 27 is a photographic image of a cross section of rodent skin.

Experimental Group PCA 50 mM 48 hours: (See FIGS. 26-27) The surface was covered with multiple layers of cells. The dermal layer was thicker. The hair follicles had double layer of cells. There was increased vascularity. Inflammation also increased in the dermis and below the muscle layer. The tissue thickness was assigned 2+.

Experimental Group C3G 100 mM

Figure 28:
FIG. 28 is a photographic image of a cross section of rodent skin.
Figure 29:
FIG. 29 is a photographic image of a cross section of rodent skin.

48 Hours: (See FIGS. 28-29) There was multiple cellular covering of the surface. The dye of the C3G was apparent on the skin surface indicating it had not changed color due to pH nor completely degraded. The dermal layer was thicker. The hair follicle had single and double cellular lining. The vascularity was prominent. There was inflammation in the dermis and muscular layer and below. The thickness of the tissue was assigned 2+.

Experimental Group C3G 200 mM

Figure 30:
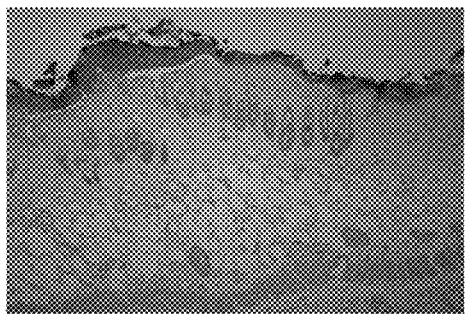
FIG. 30 is a photographic image of a cross section of rodent skin.
Figure 31:
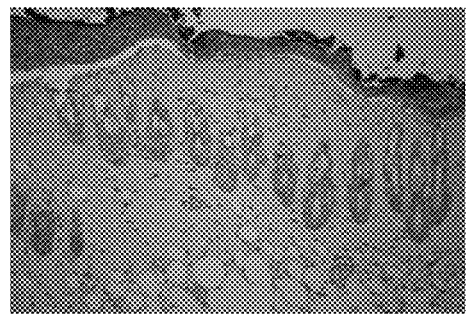
FIG. 31 is a photographic image of a cross section of rodent skin.

48 Hours: (See FIGS. 30-31) There was evidence of the C3G material remaining on the skin surface. The surface cellular layer was multiple cells thick. The dermal layer was thickened. The hair follicles had single and double cellular lining. The vascularity was increased. There was inflammation in the dermis and muscular layer. The thickness was assigned 2+.

These results confirm that an anthocyanin (~38% C-3-G as the source) and the main metabolite of anthocyanins and anthocyanidins, protocatechuic acid (PCA) when applied topically at various calculated doses to the stripped skin wound of a rodent were bactericidal in 48 to 96 hours. There was a 10,000 fold kill of *Pseudomonas aeruginosa* in 48 hours with both reagents and dose.

The results also show by histology a simultaneous healing of the experimentally created wound in the same time frame. C-3-G and PCA in two different doses stimulated tissue repair as evidence by histology.

Specifically, the experimental model provided evidence of a histological contrast between the control and experimental groups. At 48 hours, Control Group 2 that was wound stripped and infected showed a clear contrast to the uninfected Control Group 1. In the skin stripped infected group there was loss of the epithelial cellular covering, no follicular cellular proliferation, marked increase in vascularity and little inflammatory response. This histological condition provided clear contrast to the treatment groups. All treatment groups by comparison showed healing response with multiple layer cellular proliferation on the surface, multiple layer cellular proliferation along the hair follicles, less vascularity, but an inflammatory cellular response in the dermis and muscular levels. See FIGS. 14-31. PCA at a concentration of 25 mM also showed collagen layer formation between the epidermis and dermis. (See figures/photos 24 and 25). This response is beneficial in the use of anthocyanin and anthocyanidins and metabolites thereof as a cosmetic agent to promote wound healing and improve skin health, including wrinkle reduction or removal. This method of use of anthocyanin and anthocyanidin metabolites, and particularly PCA, is based upon the two fold response; the collagen layer increase and the skin swelling that increased the depth of the skin.

Example 7: PCA's Effect on *Pseudomonas Aeruginosa* ATCC 700888 and *Staphylococcus aureus* A TCC 33591 (MRSA) Biofilms The inventor has shown that a composition comprising PCA was able to stop the growth of a biofilm formation as well as destroy already formed biofilms. The biofilms tested were *Pseudomonas Aeruginosa* ATCC 700888 and *Staphylococcus aureus* ATCC 33591 (MRSA).

The following amounts were tested on a polyester cloth and sintered 316 stainless steel mesh: The cloth was a piece cut from a polyester pillow case. The cloth was soaked in the PCA solution and air dried for 24 hours. The cloth was dried when tested.

1: 20 grams of PCA in 100 ml of 70% isopropyl alcohol, vehicle: cloth material, 1-1
2: 20 grams of PCA in 100 ml of 70% isopropyl alcohol, vehicle: cloth material, 1-2
3: 20 grams of PCA in 100 ml of 70% isopropyl alcohol, vehicle: 3-ply sintered mesh, 1-1
4: 20 grams of PCA in 100 ml of 70% isopropyl alcohol, vehicle: 3-ply sintered mesh, 1-2
5: 20 grams of PCA in 100 ml of 70% isopropyl alcohol, vehicle: 5-ply sintered mesh, 1-1
6: 20 grams of PCA in 100 ml of 70% isopropyl alcohol, vehicle: 5-ply sintered mesh, 1-2
7: Glass Slide (to serve as control article), 1-1
8: Glass Slide (to serve as control article), 1-2
9: PCA crystals imbedded, vehicle: 3-ply sintered 40 micron mesh, 1-1
10: PCA crystals imbedded, vehicle: 3-ply sintered 40 micron mesh, 1-2
11: PCA crystals imbedded, vehicle: 5-ply sintered 40 micron mesh, 1-1
12: PCA crystals imbedded, vehicle: 5-ply sintered 40 micron mesh, 1-2

The bacteria (*Pseudomonas Aeruginosa* ATCC 700888 and *Staphylococcus aureus* ATCC 33591 (MRSA)) were placed in reactors and allowed to grow and form biofilms. Then cloths and metal were treated by coating with PCA solutions and then were left to dry. Two sets of the stainless steel mesh had crystals imbedded into the mesh to replicate placement into a mesh or coated joint implant. A standard ASTM E-2647 drip flow biofilm reactor was used to grow a biofilm and the treated surfaces (as well as the control) were placed into the reactors and the biofilm was allowed to grow for about 6 hours. The samples received a continuous nutrient flow for an additional time period for about 48 hours to promote a steady growth rate of the biofilm. Then the biofilm was removed, analyzed and a microbial count and log density measurements were taken for each sample. Colony forming unites ("CFU") were counted (which is an estimate of the number of viable bacterial. Log density is the calculation of the biofilm present.

It was found that A 10% concentration as not as effective against *Pseudomonas*, but a 20% concentration of PCA was very effective. See FIGS. 33 and 34. FIG. 34 shows that the materials that were treated had a very much smaller log density and CFUs than the control material (glass slide).

It was found that a 30% concentration of PCA against MRSA was very effective. See FIGS. 35 and 36.

Example 8: Spray on Solution of PCA and Time Study of PCA's Effect on *Pseudomonas Aeruginosa* ATCC 700888 and *Staphylococcus aureus* ATCC 33591 (MRSA) Biofilms Next the time necessary to destroy biofilms and kill bacteria was tested. A biofilm consisting of over 10 million organisms were formed on a glass slide. A single spray of 30% PCA mixed with isopropyl alcohol was applied to the glass slide. The colony forming units (CFU) were examined at 30 minutes and 60 minutes after the single spray. Incidentally, typical tests for testing the ability of an antibiotic to work are done for 48 hours. The tests performed were as follows:

Glass slides were inoculated at Time 0. Batch phase was performed for 6 hours to allow for biofilm formation on the glass slides. The drip flow mechanism was then turned on to provide a continuous flow of nutrients to the glass slides over 48 Hours. After 48 hours, 2 sets of glass slides were sprayed with a 30% PCA solution. One set was removed and analyzed for biofilm reduction after 30 minutes. The other set was removed after 60 minutes.

2 sets of control slides were also removed and analyzed after 30 minutes and 60 minutes. The control slides were not treated with 30% PCA and were used for comparative purposes.

The Log Reduction Calculations were performed as follows: The mean 30% PCA treated samples were compared to the mean positive control samples, per time point evaluated.

For *Pseudomonas aeruginosa*, after 30 minutes of the application of the 30% PCA spray, there was a 3.3 log reduction. After 60 minutes, there was 2.2 log reduction, which amounts to a 99.9% reduction in the number colony forming units. See FIG. 37.

For *Staphylococcus aureus*, after 30 minutes of the application of the 30% PCA spray, there was a reduction of 60 million CFUs to 3 million and after 60 minutes, there was reduction, of 25 million to 2 million CFUs. See FIG. 38.

Thus, the results show that a 30% PCA spray killed 90% of the biofilms in 30 minutes. The FDA only requires a 90% reduction.

It is noted that this above experiment was chosen to replicate a clinical condition, involving a metal or linen implant even to the extreme because there would never be that concentration of biofilms nor bacteria in practice flowing over the implants. Accordingly, the invention also provides a method of blocking initial attachment of the bacteria to the implant and therefor preventing growth/development of a biofilm on an implant.

It was determined that the effective amount of an anthocyanin, anthocyanidin or metabolite thereof (e.g., PCA or 2,4,6 THBA) depends upon the species of bacterial to be eradicated. It was discovered that a 10% concentration of PCA was not effective on *Pseudomonas aeruginosa* (see FIG. 33), whereas a 20% concentration was effective (see FIG. 34).

The biofilms destroying properties of coating metal and linen for Methicillin resistant *Stapylococcus aureus* required higher dose than *Pseudomonas aeruginosa* (see FIG. 35). At a concentration of 30%, it was effective (see FIG. 36). The application on an implant allowed to dry had the above results. However, when a glass surface is covered with 10 million biofilms colonies the results differ with the concentration and the bacteria biofilms to be eradicated. The glass surface experiments are described in example 8. Generally, Glass slides were inoculated at Time 0. Batch phase was performed for 6 hours to allow for biofilm formation on the glass slides. The drip flow mechanism was then turned on to provide a continuous flow of nutrients to the glass slides over 48 Hours. After 48 hours, 2 sets of glass slides were sprayed with a 30% PCA solution. One set was removed and analyzed for biofilm reduction after 30 minutes. The other set was removed after 60 minutes. 2 sets of control slides were also removed and analyzed after 30 minutes and 60 minutes. The control slides were not treated with 30% PCA and were used for comparative purposes. The Log Reduction Calculations were performed as follows: The mean 30% PCA treated samples were compared to the mean positive control samples, per time point evaluated. The results were as follows for a single spray of 30% PCA in isopropyl alcohol on 10 million biofilms colonies of *Pseudomonas aeruginosa*. See FIG. 40. The concentration of 30% has lesser effect on MRSA, but still 90%. See FIG. 41. These experimental concentrations of biofilms covered pathogens that far exceed the concentrations and numbers found in practice.

Example 9: Testing Against *Propionibacterium acnes*

BALB/c mice were infected with *Propionibacterium acnes* via intradermal injection and treated topically with varying concentrations of a novel test compound, PCA, at 2, 24, 48 and 72 hours following challenge. Efficacy was evaluated by CFU analysis from skin samples harvested at 96 hours post challenge.

These data demonstrate that *P. acnes* establishes a steady intradermal colonization in the skin of BALB/c mice. When administered topically, PCA at 60 mg/kg, demonstrated a bacteriostatic effect and reduced *P. acnes* CFU burden in mouse skin by a statistically significant amount. All lower amounts of PCA showed no such effect.

Female BALB/c mice, ordered from Harlan and weighing 17-19 g, were acclimated to housing conditions and handled in accordance with AUP number TP-18-13. The animals were acclimated for 4 days prior to bacterial challenge. Only animals deemed healthy and fully immunocompetent were included in this study. Cages were prepared with 2 mice per cage.

The animals were fed Teklad Global Rodent Diet (Harlan) and water ad libitum. Mice were housed in static cages with Teklad ⅛" corn cob bedding inside bioBubble® Clean Rooms that provide H.E.P.A filtered air into the bubble environment at 100 complete air changes per hour. All treatments and infectious challenges were carried out in the bioBubble® environment. The environment was controlled to a temperature range of 74°±4° F. and a humidity range of 30-70%. Treatment groups were identified by cage card. All procedures carried out in this experiment were conducted in compliance with all the laws, regulations and guidelines of the National Institutes of Health and with the approval of the TransPharm Animal Care and Use Committee.

Bacterial Cultures

*Propionibacterium acnes* (1100; ATCC 6919), procured directly from the American Type Culture Collection.

Skin Preparation

On Day −1, each mouse was anesthetized in an Isoflurane induction chamber and the lesion site was cleared of hair. An area of approximately 2.0 cm×2.0 cm of skin on the dorsal area of each mouse was cleared through use of the depilatory agent Nair®.

Challenge

Cultures were grown for 96 hrs at 37° C. in an anaerobic atmosphere on TS agar plates supplemented with 5% sheep blood cells. The culture was aseptically swabbed and transferred to tubes of TS broth and allowed to grow for 72 hours. The cultures were diluted to provide challenge inoculum of approximately 6.0-7.0 log 10 CFU per 50 µL in PBS. On Day 0 each mouse was anesthetized using Isoflurane. Each animal on the study was administered 50 µL of the bacterial suspension via intradermal injection in the dorsal area that was previously denuded of hair. The final CFU count from the challenge suspension determined that 6.0 log 10 CFU per mouse were delivered.

Formulation and Dosing

The test treatment, PCA, was provided by the study Sponsor and formulated using sterile water. Treatments were administered topically in a dose volume of 0.1 mL. Treatments were given at 2, 24, 48 and 72 hours post challenge at 60 mg/kg (78 mM; Group 3), 30 mg/kg (39 mM; Group 4) or 15 mg/kg (19.5 mM; Group 5).

At 96 hours following challenge, mice were humanely euthanized and skin was aseptically removed from the infection site. Skin samples were placed in homogenation vials with 2.0 mL PBS, weighed and homogenized using a mini-bead beater. Homogenate was serially diluted and plated anaerobically on TSA agar plates for enumeration of colony forming units per gram of skin tissue.

Figure 39:
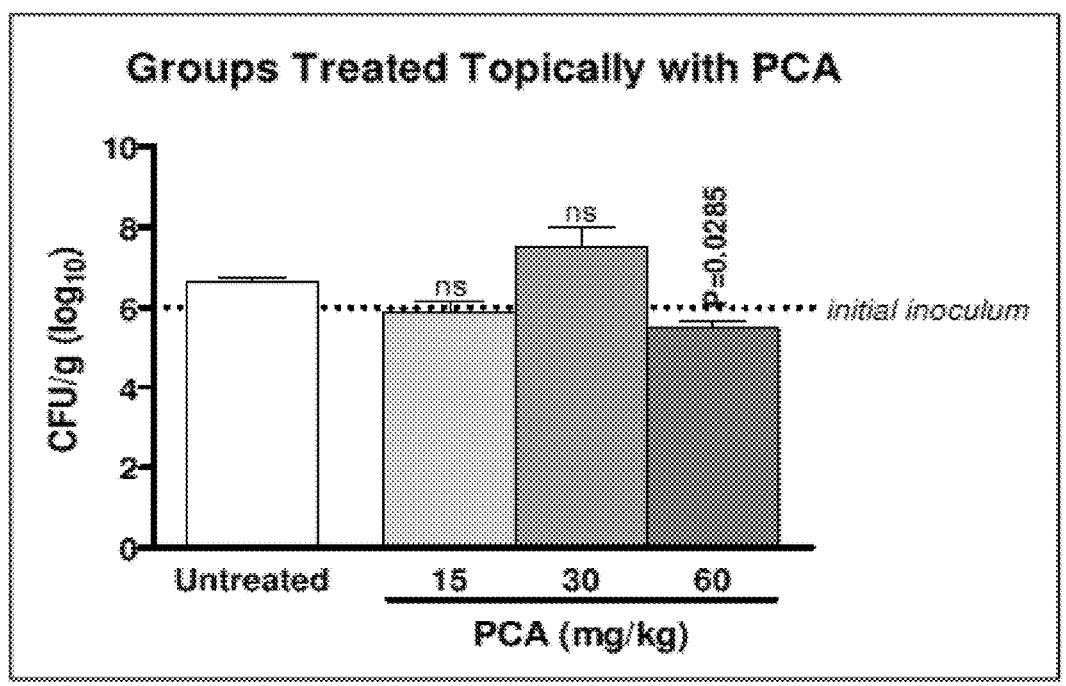
FIG. 39 provides a chart of results of testing PCA against *P. acnes* on the skin.

The mean bacterial burden of the untreated group at 96 hours was 6.65 log 10. CFU levels in all treated groups were compared to the untreated group to determine statistical significance. Only the high dose of PCA (60 mg/kg) showed significant reduction of CFU burden when compared to the untreated control (P=0.0285). That an approximately 1 log 10 reduction was observed indicates that at this concentration PCA, is bacteriostatic and not bactericidal. All other treatments were statistically non-different than the untreated control (FIG. 39).

These data demonstrate that *P. acnes* establishes a steady intradermal colonization in the skin of BALB/c mice. When administered topically, PCA at 60 mg/kg (78 mM solution), demonstrated a bacteriostatic effect and reduced *P. acnes* CFU burden in mouse skin by a statistically significant amount. All lower amounts of PCA showed no such effect.

Example 10: Antibiotic Testing with PCA or 246 THBA Using Propylene Glycol

PCA or 246 THBA were combined with propylene glycol (PPG). The PPG was placed on a paper disc and then either PCA or 246 THBA was applied. The paper disc was then placed on colonies of various bacterial in a Petri dish. At a certain uniform time they were inspected and classified in the following categories:

NI: no inhibition of bacteria growth under the sample
I: inhibition of bacterial growth under the sample
NZ: no accompanying zone of inhibition
CZ: clear zone of inhibition surrounding the sample and zone measured in millimeters (mm).

TABLE 1

Animal Challenge, Treatment and Harvest Schedule

| Group | n | Intradermal P. acnes | Treatment | ROA | Schedule | CFU harvest* |
|---|---|---|---|---|---|---|
| 1 | 2 | 6.0 log | untreated | NA | NA | 2 hr |
| 2 | 2 | 6.0 log | untreated | NA | NA | 96 hr |
| 3 | 2 | 6.0 log | PCA 60 mg/kg | Topical | 2, 24, 48, 72 hrs | 96 hr |
| 4 | 2 | 6.0 log | PCA 30 mg/kg | Topical | 2, 24, 48, 72 hrs | 96 hr |
| 5 | 2 | 6.0 log | PCA 15 mg/kg | Topical | 2, 24, 48, 72 hrs | 96 hr |

*Relative to Challenge at 0 hr

Results and Discussion

Infection/Treatment/General Observations

None of the study subjects displayed any acute adverse events associated with the treatments. None of the test subjects succumbed to the infection or showed signs of morbidity, which could be attributed to penetration of the infection into the circulatory system or deep tissue. No treatment group displayed adverse signs beyond those expected for mice which have received a superficial bacterial infection.

The test article preparations were administered topically at 2, 24, 48 and 72 hours following the bacterial challenge. While untreated mice were harvested at 2 hours post infection, CFU burden was not detected. However at 96 hours post infection, the CFU burden rose from 6.0 log 10 to 6.65 log 10, indicating a successful inoculation.

The results were as follows:
Water/PCA/*Klebssilla pneumonia* ATCC4352: I/CZ/2 mm
PPG/PCA/*Klebssilla pneumonia* ATCC4352: I/CZ/3 mm
Water/PCA/*Pseudomonas aeruginosa* ATCC9027: I/CZ/10 mm
PPG/PCA/*Pseudomonas aeruginosa* ATCC9027: I/CZ/4 mm
Water/246 THBA/*Pseudomonas aeruginosa* ATCC9027: I/CZ/2 and 3 mm
PPG/246 THBA/*Pseudomonas aeruginosa* ATCC9027: I/CZ/3 mm
Water/246 THBA/*Staphylococcus aureus* ATCC33591 (MRSA): I/CZ/14 and 15 mm
PPG/246 THBA/*Staphylococcus aureus* ATCC33591 (MRSA): I/CZ/12 mm

Example 11: PCA to Sterilize/Disinfect Human Skin Study

A randomized double blinded study was performed at Loma Linda Medical School. It involved 4 phases over two years' time. The methods were as follows:

Phase 1: The active test reagent was topically applied 1.54% PCA in sterile water to the anterior shoulder region. This 1.54% solution of PCA in water was used effectively in our prior animal wound studies. The controls were Chloraprep (2% Chlorhexidine in 70% isopropyl alcohol) and Betadine (9.0% to 12.0% available iodine in water). Cultures were taken before application and 20 minutes after application. The initial harvest was by a surface swab. Application was by soaked sponge, without force or scrubbing. The second harvest was performed with the back edge of a sterile knife blade scraping with pressure in attempt to maximize the harvest from the deeper sebaceous glands and hair follicles. The specimens were placed in culture media. Bacteriology was performed at WuXiAppTec in Marrietta, Ga.

Phase 2 included eleven medical students and was same method as Phase 1. However the PCA vehicle was changed to 70% isopropyl alcohol. This allowed a higher concentration of PCA than possible in sterile water, 10%. Phase 2a: The 70% isopropyl alcohol vehicle was tested for its bactericidal properties. All cultures that were negative or markedly reduced with PCA topical solution were examined for exact nature of the index bacteria and the post treatment cultures that showed no or minimal growth. In this way it was learned what specific bacterial strains PCA could eliminate or reduce.

Results:

Phase 1 showed the aqueous solution of 1.54% PCA to be partially effective as compared to the controls. In phase 1 of the Loma Linda Studies, 1% PCA in water showed no growth in 7 of 22 subjects on aerobic culture and 10 cultures showed reduced growth. By anaerobic culture, 6 of 22 cultures showed no growth and 15 showed reduced colony growth. Six heavy growth pre-treatment cultures prior to the 1.24% PCA treatment were chosen to examine the isolates to learn what pathogens were killed or not killed. Most of the bacteria eradicated were non pathogens. Sample culture #29 showed 5 unique colonies by aerobic culture and 2 unique colonies by anaerobic culture. After 1.24% PCA treatment there was no growth on either culture. Therefore pre-treatment cultures were examined for the species. The chart below is the result of the specific species colony identified and the method of identification used. The organisms were predominately non pathogens except for *P. acnes*. However all of which were removed by the treatment.

Two other index pre-treatment cultures showed heavy growth of *Propionibacterium acnes*, a potential pathogen. The post treatment cultures showed the colonies of *P. acnes* was decreased to 5 colonies in one and 1 colony in another, but not eliminated. This suggested that PCA may be effective against *P. acnes* if a higher concentration was applied in subsequent Phases of this study. Testing with 1.24% in water killed bacteria of normal flora as shown above chart. To increase efficacy and to improve skin penetration to the depth of the hair follicles that can harbor bacteria, Phase II of the study used 70% isopropyl alcohol (30% water) 85 ml so as to increase the concentration of PCA.

Phase II:

This study involved 11 human subjects. There were 5 Males and 6 females. The ages were 23-33 years. There were two reagents. The control was 70% isopropyl alcohol. The PCA source was a phytochemical extract from Nanjing Zelang Medical Technology Co. LTD. This source was chosen due to markedly reduced cost of goods compared to that which is biochemically manufactured. The experimental dose was 9+/−% PCA in 70% isopropyl alcohol. 10 grams of PCA was placed in 100 ml of isopropyl alcohol. The isopropyl alcohol allowed for a greater dose of PCA than water. (allowed more PCA to be dissolved). The initial harvest was by a surface swab. Application was by soaked sponge, without force or scrubbing. The second harvest was performed with the back edge of a sterile knife blade scraping with pressure in attempt to maximize the harvest from the deeper sebaceous glands and hair follicles.

Cultures were stored in ice and shipped in FedEx ice box to WuXiapptec in Marietta, Ga. for aerobic and anaerobic cultures and held for 21 days. Method used for bacterial species identification was Vitek® MS-MALDI-TOF MS. It was determined that the dose or concentration of PCA needed to be increased, which required changing the water to 70% isopropyl alcohol. This is the same as used with Chloraprep® which is 2% w/v chlorhexidine gluconate in 70% isopropyl alcohol. 10% PCA in 70% isopropyl alcohol was compared to the control 70% isopropyl alcohol in Phase II. The results of Phase II showed the following summary of the no growth culture results after treatment.

|  | Aerobic | Anaerobic |
| --- | --- | --- |
| PCA/IP alcohol | 10/11 no growth | 9/11 no growth |
| Control IP alcohol | 6/11 no growth* | 4/11 no growth |

*Note that 3/11 of the 70% IPA groups showed increased colony growth after IPA treatment alone.

Phase 2 results with 9+% solution of PCA were compared to similar test Phase 1 and this showed this to comparable to Betadine in effectiveness, but not with Chloraprep, which killed all the bacterial colonies. This PCA/70% isopropyl alcohol solution was effective against 10/11 index cultured aerobic bacteria and reducing on anaerobic culture in 9 of 11 subjects. The two showing residual colonies were one (n=1) colony of *Propionibacterium acnes* in each of the two cultures. Phase 2a showed that 70% isopropyl alcohol (IPA) alone had few antibacterial properties. Of course sterile

| SAMPLE ID | GRAM STAIN & CELL MORPHOLOGY | ORGANISM IDENTIFICATION | METHOD OF IDENTIFICATION |
| --- | --- | --- | --- |
| 1(A) | Gram positive cocci | *Micrococcus luteus*/lylae | Biochemical Analysis |
| 1(B) | Gram positive cocci | *Micrococcus luteus*/lylae | Biochemical Analysis |
| 1(C) | Gram positive cocci | *Micrococcus luteus* | Biochemical Analysis |
| 1(D) | Gram positive cocci | *Micrococcus luteus* | Biochemical Analysis |
| 1(E) | Gram positive cocci | *Staphylococcus epidermidis* | DNA Sequencing |
| 2(A) | Gram positive cocci | *Staphylococcus capitis* | Biochemical Analysis |
| 2(B) | Gram positive rods | *Propionibacterium acnes* | DNA Sequencing | water used in Phase 1 had no antibacterial properties, therefore the testing was on the effectiveness of the PCA.

The Phase 2 study showed the importance of PCA reagent concentration or dose. A different application necessitated an increase dose. PCA at 1.54% although effective in an animal open skin wound was not a very effective antibacterial reagent on intact human skin. Therefore the concentration of PCA needed to be increased and could not be increased with water, but only be accomplished with the vehicle of 70% isopropyl alcohol.

Phase 2 showed that PCA was more effective in the higher concentration eliminating all bacteria and reducing *Propionibacterium acnes* to one colony in two separate instances. It should be noted that the 70% isopropyl alcohol vehicle had little anti-bacterial properties. The water was sterile and the alcohol tested negative in vitro. Therefore, they did not contribute other than as a vehicle for topical application in this environment.

The interval of 20 minutes was chosen for testing was similar to what would be expected if used as a surgical preparation.

The first and 2nd method of harvesting differed. The 2nd was accomplished with pressure wiping with the back end of a sterile scalpel so as to maximize the harvest even from sub surface sweat gland and hair follicles.

The strengths of this study were in the careful attention given to the method to disadvantage the topical applications effectiveness, yet PCA was effective and comparable to Betadine tested similarly as Phase 1. The PCA used was a single molecule of 99% pure biochemically synthesized PCA. The water an and the isopropyl alcohol could be discounted as a contributor to the effect as it contributed nothing to the bactericidal effect; sterile water and null effect of IPA in vitro testing.

The method used placed a burden on effectiveness of the reagents by the short time (20 minutes) to act and the 2nd harvest maximizing the potential yield due to the pressure scraping with back edge of a scalpel.

This study showed the effectiveness of a single reagent, PCA, the common phytochemical metabolite. It showed that a single concentrated metabolite working alone is bactericidal on human skin. It showed the importance of dose variation depending upon the intended topical application; wound versus intact skin. It showed the effectiveness absent any potential antibacterial boost from the isopropyl alcohol vehicle.

It established the criteria necessary for consideration as a drug; single reagent, known dose effective in two different host environments, topical application route, frequency of application (once), duration (20 min) time to gain the intended result.

Phase 3: Another test was conducted where the PCA was dissolved in 15 ml propylene glycol. The PPH is a skin penetration enhancer and assists in dissolving PCA.

In another test, 5 ml of essential oil of Peppermint was added. This has skin penetration enhancer properties and anti-microbial properties.

Based upon Phase I and II results, it was determined that the dose or concentration of PCA should be increased. It also was determined that it would be ideal to have something in the composition that possessed skin penetration properties. Therefore propylene glycol (PPG) was added. Fasano W J, ten Berge W F, Banton M I, Heneweer M, Moore N P. Dermal penetration of propylene glycols: measured absorption across human abdominal skin in vitro and comparison with a QSAR model. *Toxicol In Vitro*. 2011 December; 25(8): 1664-70. Then to further the skin penetration an essential oil was added; i.e. an essence of peppermint oil (EOPO) (Nature oil, 1800 Miller Parkway, Streetsboro, Ohio 44241 100% pure [Japan]. Chen J, Jiang Q-D, Wu Y-M, Liu P, Yao J-H, Lu Q, Zhang H, Duan J-A. Potential of Essential Oils as Penetration Enhancers for Transdermal Administration of Ibuprofen to Treat Dysmenorrhoea Molecules 2015, 20, 18219-18236. Note that both PPG and EOPO are skin penetration enhancers but also have antimicrobial properties. *P. acnes* normally reside deep in the skin's hair follicles and or sebaceous glands. Therefore non-penetration common commercial disinfectants are not effective as reported in the literature and noted in the Background section above.

The composition of matter was created when 20 grams of PCA was placed in 85 ml 70% isopropyl alcohol making a concentration of PCA 17% (+/−). Then 15 ml propylene glycol and 5 ml of essential oil of peppermint were added. All reagents had skin penetration properties. The opposite shoulder had only the control 70% isopropyl alcohol vehicle applied. The subjects volunteered they liked the peppermint smell. The following summary is the no growth culture results after treatment.

| Reagent | Aerobic | Anaerobic |
|---|---|---|
| 17% +/− PCA composition | 10/12 | 11/12 |
| 70% IPA alone | 10/12 | 8/12 |

The analysis of the 2 pre PCA treatment subjects that grew subsequent positive cultures were analyzed as follows:

PCA Pre Treatment Aerobic Species Analysis:

The index subject #18 aerobic growth was too numerous to count. There were 2 different species; *Staphylococcus epidermidis/hominis* and *Micrococcus luteus*. The Subject #18's post PCA treatment aerobic culture, #20 showed 2 colonies; *S. capitis* and *S. epidermidis*. For reasons unknown, neither of these species was identified in the index culture, and both are considered non pathogens. The pre-PCA treatment index culture on subject #37 had colonies too numerous to count (TNTC) with heavy growth. The colony species were reported as one; *Staphylococcus capitus*. The Subject #37's post PCA treatment aerobic culture #39, showed one (1) colony growth, but not the former *S. capitus*, but was identified *Staphylococcus epidermidis* as the residual. As in prior phases, the residual growth was most often a non pathogen on aerobic culture.

Anaerobic Species Analysis:

The 17% PCA composite solution resulted in 11 of 12 subject's subsequent cultures having no growth. Pre PCA treatment subject #18 had bacteria colonies too numerous to count (TNTC) on anaerobic culture. There were 4 separate colonies with the following species; *S. epidermidis* (n=3) and *Propionibacterium avidium*. After this PCA treatment there was no anaerobic growth. Subject #37 index anaerobic culture showed 79 colonies. There were 4 prominent colony species; *Staphylococcus epidermidis, Staphylococcus capitis/caprae, Staphylococcus capitis* and *Propionibacterium acnes*. The one post PCA culture that showed a bacterial colony culture was subject #37 with post PCA treatment anaerobic culture being #39. There were 2 two colonies of same species; *Staphylococcus epidermidis*. There were no *Propionibacterium acnes* colonies. Thus, the results of Phase 3 showed the effectiveness of 17%+/−PCA in a composition of matter that had skin penetration properties; propylene glycol and essence of peppermint oil.

In Phase IV the method was different from the previous phases:

Method:

The variations in materials and methods in this phase were based upon results of the previous phases. They included changes in the solution, the method of dissolving the PCA, the timing of skin application, plus using two applications to simulate the present day recommendations of surgical skin preparation.

The solution used was 20 mg of ground PCA (Nanjing Zelang Medical Technology Co. Ltd.) in 95 ml 91% isopropyl alcohol and 5 ml of essential oil of peppermint 100% pure. The method placed the 20 grams of ground PCA in sterile container with volume markers. Then added 85 ml of 91% isopropyl alcohol; warm and shake. 5 ml of essential oil of peppermint was added. A repeat of warming and shaking was instituted. The container was filled to 100 ml, warm and repeated the shaking. It took perhaps 15 to 20 minutes for the ground crystals to dissolve.

An area was marked at 4 corners on the anterior axilla area of both shoulders. There was a topical reagent application. After 5 minutes a second application was made. The control group was again Chloraprep®. The experimental side was applied with manual motion and pressure on a sterile sponge soaked with the PCA solution. The subjects put hands on head for 10 minutes and then 10 minutes of moving arms around. Culture #1 was harvested with scraping at 20 minutes post $2^{nd}$ application. Subjects rested their arms at side for 40 minutes which is 60 minutes after the first application and 40 minutes after culture #1. A second culture is taken with scraping. The post application cultures were taken of each shoulder skin area with scraping with back side of a sterile surgical knife blade to maximize the yield.

Results of Phase IV:

The index pre-treatment culture's average colony counts of the 4 groups were similar.

|  | Aerobic | Anaerobic |
| --- | --- | --- |
| PCA | 34.4 average | 44.4 average |
| Chloraprep ® | 41.75 average | 49.83 average |

The only group showing no growth in all 12 treated subjects was the PCA/peppermint solution treated aerobic group at 20 minutes. Other than that group, neither PCA nor Chloraprep® sterilized the skin 100% at 20 or 60 minutes. However, Chloraprep® had more "no growth" cultures in total. The following summary is the no growth cultures results after treatment.

|  | Aerobic | anaerobic |
| --- | --- | --- |
| PCA 20 minutes | 12/12 | 4/12 |
| PCA 60 minutes | 7/12 | 6/12 |
| Chloraprep ® 20 minutes | 10/12 | 8/12 |
| Chloraprep ® 60 minutes | 10/12 | 10/12 |

The 20% PCA in 91% IPA and PPO was most effective at 20 minutes on aerobic culture, but not otherwise. Chloraprep® was partially effective at 20 minutes and maintained similar effectiveness on aerobic culture and same effectiveness on anaerobic cultures at 60 minutes. The results were different on Chloraprep at 20 minutes from Phase 1 when there was no growth following this reagent application.

There were 9 cultures that warranted selection for species determination. #8 pre PCA treatment anaerobic culture had 8 colony count but zero at 20 and 60 minutes. The interest was to learn what bacterial were eliminated. There were two species; S. capitis and S. epidermidis. #12 post PCA at 60 minutes showed 1 spreader colony on the plate (SPR) 50 colonies. This contrasted with the pre-treatment of 28 colonies. The species found in #12 aerobic were Klebsiella pneumonia/oxytoca and Micrococcus leuteus. These are not common pathogens. #14 pre PCA anaerobic showed 115 colonies. The species were Propionibacterium acnes, S. lugdunensis and Kocuria varians. There was no growth at 20 minutes showing that potential pathogen P. acnes was eliminated. However, there were 4 aerobic colonies at 60 minutes in #19. They were Gram Negative Rods: Stenotrophomonas maltophilia: rare pathogen and Stenotrophomonas maltophilia. The Gram Positive cocci were Kytococcus sedentarius: rare opportunistic pathogen and Micrococcus luteus/lylae: opportunistic pathogen, particularly in hosts with compromised immune systems, such as HIV patients. #19 was a pre PCA anaerobic culture with 39 count showing species of P. acnes and S. epidermidis. #21 was the post PCA at 20 minutes and showed 1 anaerobic colony of P. acnes, a reduction from 39 colonies.

There was culture of Gram Positive Rods with spores identified as: Lysinibacillus sphaericus/fusiformis: rare pathogen. #23 showed no growth at 60 minutes for aerobic or anaerobic. Therefore all aerobic bacteria including the one anaerobic colony of P. acnes was gone at 60 minutes. #31 aerobic was pre PCA showing 134 colonies. The species were Micrococcus luteus and Micrococcus luteus/lylae. There was no growth at 20 or 60 minutes of these normal flora species. #31 anaerobic was a pre PCA showing 28 colonies of Staphylococcus lugdunensis and Bacillus cereus/thuringiensis. There was no growth of either at 20 and 60 minutes. #32 was pre Chloraprep with aerobic colony count of 59 with the following species: Micrococcus luteus/lylae, Micrococcus luteus and Kocuria Kristinae. There was no colony growth at 20 or 60 minutes. #32 was pre Chloraprep anaerobic with 17 colonies with the following species: S. epidermidis and Gemella Bergeri/sanguinis. The post treatment showed no growth at 20 or 60 minutes. It should be noted in any of the literature or these experiments that re-colonization occurs with skin bacteria, likely in 30 minutes after treatment.

Species Analysis:

The pre-treatment species were predominately saprotrophic or commensal organisms. Propionibacterium acnes was identified in two subjects. After PCA treatment the specific species analysis showed predominately saprotrophic or commensal organisms. The potential pathogen Propionibacterium acnes was identified with 19 colonies pre-PCA treatment in #14 but showed no growth at 20 minutes after PCA treatment. P. acnes was identified pre-PCA treatment in #19 with 19 colonies and post treatment at 20 minutes there was one remaining colony of P. acnes. However, there was no growth at 60 minutes.

Discussion of Phase IV:

This solution of 20 grams of PCA, 75 ml of 91% isopropyl alcohol and 5 ml of essence of peppermint oil was effective in removing potential pathogens, including Propionibacterium acnes. Only commensal bacteria with rare pathogenicity remained. The control Chloraprep® did not removed most of the bacterial colonies, but not all. Many saprotrophic or commensal organisms were left intact. The PCA composition was not as effective as Chloraprep® against anaerobes, but where there was post PCA growth the species-specific analysis showed that *Propionibacterium* was controlled.

A composite of the results based only no growth cultures following treatment by each solution are shown in FIG. 42. *Note that the 1% PCA was not included. The summation percentages of "no growth" are shown in FIG. 43.

Summary of the 4 Phase Testing at Loma Linda:

The questions proposed in the purpose of this proof of principle pilot study were answered in the affirmative. The optimal dose of PCA to act as a human skin disinfectant is greater than 10%. There is a facilitating delivery vehicle, which is at least 70% isopropyl alcohol, which allows higher concentrations of PCA to go into solution than water, propylene glycol and or essential oils alone. The results were optimized by the addition of known skin penetration enhancers; propylene glycol and essence of peppermint oil. *P. acnes* normally resides deep in the skin's hair follicles and or sebaceous glands. Therefore, non-penetration common commercial disinfectants are not effective.

PCA in one or more of these vehicles provided a broad-spectrum disinfectant effect comparable to existing commercial products; isopropyl alcohol, Chloraprep® and Betadine®.

One of two result assessment approaches was considered in this study. One is related to government regulations and is called non-inferiority status, or the showing the test article is essentially the same as a marketed product. The reason to choose this method is that the existing marketed products in the study had side effects, complications, and or higher cost. D'Agostino Sr R B, Massarol J M, Sullivan L M. Non-inferiority trials: design concepts and issues—the encounters of academic consultants in statistics *Statist. Med.* 2003; 22:169-186.

The other method is to establish clear superiority to an existing product. Both were considered in this study. The various PCA solutions showed a non-inferiority status to 70% Isopropyl alcohol, Betadine® and Chloraprep®. The PCA solutions in this study showed superiority to all but Chloraprep®. After the first Phase and each subsequent Phase results, the materials and methods were modified in attempt to improve the results of the test reagent PCA. The vehicle was changed from water to isopropyl alcohol to facilitate an increase dose of PCA. In addition, the vehicle was change to include reagents known to have skin penetration properties as well as antibiotic properties; i.e. propylene glycol and essence of peppermint oil. In Phase III, the best PCA results in both aerobic and anaerobic cultures were obtained with a mixture of 17% PCA, propylene glycol and essence of peppermint oil. The anaerobic cultured bacteria are those likely to be below the skin surface and perhaps were affected by the addition of the skin penetrator enhancing reagents. PCA effectiveness was demonstrated in Phase I, even with the low dose of a 1.24% aqueous solution. This aqueous solution of PCA decreased the colonies of *Propionibacterium acnes* that were too numerous to count down to about to 1 and 5 colonies on same subject after treatment. Solutions of PCA at 10% or higher removed all pathogens, including *P. acnes*, but not all bacteria. Based upon the literature and the results of this study, the goal of complete sterilization of the human skin may not be possible, predictable or desirable. In fact, sterilization may not be desirable as it may eliminate bacteria that are beneficial to skin health and homeostasis. It does seem reasonable to remove all bacteria species that have pathologic potential. The irony of this goal is that it is reported that *Propionibacterium acnes* although in some instances has become a pathogen, it also has beneficial properties secreting a novel antioxidant. PCA, which decreased and or eliminated *P. acnes* in these studies, is an anti-oxidant so its presence as such may substitute for the biological anti-oxidant benefit of *P. acnes*. To further confuse any such study of this nature, it has been reported that the amount of bacteria on the skin prior to surgery are not directly related to surgical site infection. (Cronquist A B, Jokob K, Lai L, Latta P D, Larson E L. Relationship between Skin Microbial Counts and Surgical Site Infection after Neurosurgery. Clin Infect Dis. (2001) 33 (8):1302-1308).

In Phase I, Chloraprep® showed sterilization of the skin in all subjects. However, this was not replicated in Phase IV at 20 minutes or at the extended time of 60 minutes. It should be noted that Saltzman, et al reported in the literature that Chloraprep® had a 7% incidence of residual bacteria; *Propionibacterium acnes* and *Staphylococcus aureus* persisted after treatment and his harvest was at a short time in which the reagent was still moist and there was not enough time perhaps for recolonization. (Saltzman M D, Nuber G W, Gryzlo S M, Mareck G S, Koh J L. Efficacy of Surgical Preparation Solutions in Shoulder Surgery. J Bone Joint Surg Am, 2009 Aug. 1; 91 (8): 1949-1953). There is no clear reason for the difference in Chloraprep® results in the literature since there were many variables in methods and timing of harvesting. There is not an apparent explanation for the differing results at 20 minutes in Phase I and IV in our study. Yet in Phase IV Chloraprep® was better than 20% PCA in 91% isopropyl alcohol and 5 ml of essence of peppermint oil except at 20-minute aerobic cultures, which were sterile with the PCA solution. Note that isopropyl alcohol was not in Phase IV solution.

Another measure of a treatment method would be the effectiveness to reduce bacteria colony counts. This was common with PCA solutions in all phases. A reduction in bacteria is a well-known principle in surgery in order to reduce the chance of infection. (Anglen J. Perspectives on Modern Orthopedics. Wound Irrigation in Musculoskeletal Injury. J Am Acad Ortho Surg. July/August 2001. 9 (4). 219-226).

Figure 8A:
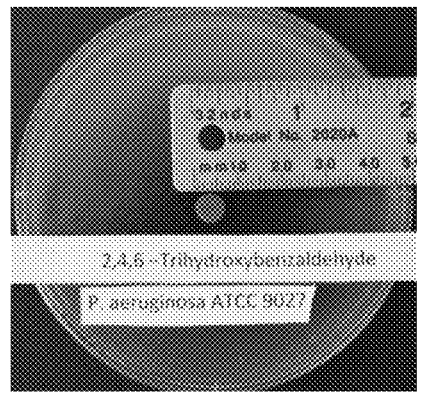
FIG. 8A is a photographic image illustrating in vitro test results of 2,4,6 THBA against *P. aeruginosa*.
Figure 8B:
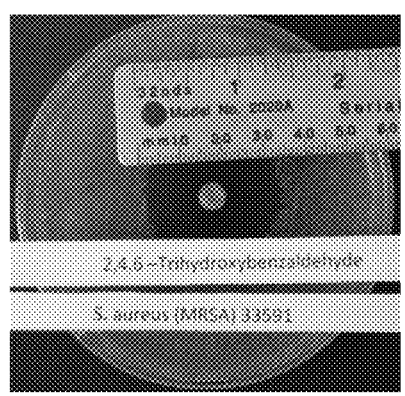
FIG. 8B is a photographic image illustrating in vitro test results of 2,4,6 Trihydroxybenzaldehyde against *S. aureus* 33591 (MRSA).
Figure 8C:
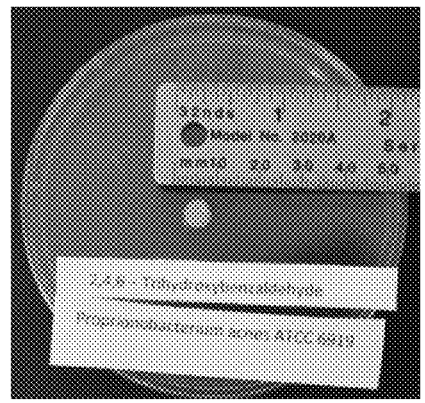
FIG. 8C is a photographic image illustrating in vitro test results of 2,4,6 THBA against *P. acnes*.

The identification of anthocyanins and anthocyanidins or combinations of anthocyanins, anthocyanidins or their metabolites that are bactericidal or antimicrobial was determined by conducting in vitro testing described above. Anthocyanidins that were tested at 100 mM (44.938 grams per liter) with less than one milliliter per dose included delphinidin, pelargonidin, and cyanidin CI and cyanidin-3-glucoside. Protocatechuic acid and 2, 4, 6 trihydroxybenzaldehyde, the anthocyanidin metabolites, were also tested at the same concentrations. Referring to FIGS. 6-8, delphinidin limited growth against *C. perfringens*, *S. aureus*, and MRSA. Pelargonidin limited growth of *P. acnes*, *C. perfringens*, *S. aureus*, MRSA, and *S. pyogenes*. Cyanidin CI was effective against *C. difficile*, *C perfringens*, *S. aureus* ATCH 6538, *S. aureus* (MRSA) ATCH 33591, *S. mutans*, and *S. pyogenes*. C3G (approximately 28% by weight) had limited effectiveness during this study (18-24 hours for aerobes; 48 hours for anaerobes (*C. albicans* and *L. casei*). This proprietary C3G formulation, however, was effective against *P. acnes, E. coli*, MRSA, *K. pneumoniae* and *P. aeruginosa*. Protocatechuic acid (PCA), the main metabolite from anthocyanins and anthocyanidins, was effective against all bacteria tested as well as *C. albicans* and *K. pneumonia*. Importantly for skin wound treatment, PCA was effective against *S. aureus* 6538 and 33591 (MRSA) and *P. aerugi-*

*nosa*. PCA was also effective on *C. albicans*, which is important considering its ability to form biofilms and difficulty in treating *C. albicans* when existing with a catheter or implant. 2, 4, 6 Trihydroxybenzaldehyde was effective against *E. coli, K. pneumonia, P. aeruginosa, S. aureus* 6538 and 33591 (MRSA); it also was effective against *A. pullulans*, ATCC 15233, a fungi.

While specific dosages of certain anthocyanins and anthocyanidins were determined to have the above mentioned effects against certain bacteria, in vivo testing were conducted to determine optimal dosages and to confirm the ability of a topical application of these compounds to have antimicrobial effect while prompting healing of a wound. It was hypothesized that certain dose and interval topical application of a water soluble solution of PCA and/or C3G (28% of C3G by weight) at certain concentrations based upon molecular weight would kill or reduce the bioburden of *Pseudomonas aeruginosa* while healing the wound as evidence by optimization of the local growth hormones and confirmed by histological evidence. Referring to FIG. 9, a decrease in bacterial burden in the skin at 96 hours days was noted (CFU means colony forming units). A concentration of 50 mM of PCA was found to be most effective; higher concentrations of PCA were not as effective at decreasing bacterial burdens. The most effective concentration of C3G was 100 mM. Importantly, histological evaluations of skin samples from the study confirmed healing at 48 and 96 hours with proliferation of parafollicular cells and migration to cover the skin surface. There was minimal inflammation in the dermis. There was collagen proliferation in the dermis.

As provided in FIG. 1, bacteria have a range of pH at which growth is optimized, and most bacteria are more viable at basic pH ranges. Generally, anthocyanins, anthocyanidins and their metabolites also have an acidic pH and have the potential to have bactericidal or bacteriostatic modes of action. Because C3G and PCA reagents have an acidic pH, their bactericidal or bacteriostatic mode of action is by direct contact with the bacteria.

Anthocyanins and anthocyanidins were further studied to determine effects on wound healing, including whether they had any effect on the optimization of local growth hormone activity at the wound site along with other supporting histological evidence of promoting healing.

Local growth hormones are important substances in the control of wound healing. Equally as important, however, is to optimize the amount of these hormones desirable for promoting wound healing while avoiding scar formation and keloids.

Examples of common local growth hormones related to skin wound healing include Epidermal growth factor (EGF), Insulin-like growth factor-1 (IGF-1) and Transforming Growth Factor-Beta (TGF-β). Epidermal growth factor or EGF is a growth factor that stimulates cell growth, proliferation, and differentiation by binding to its receptor EGFR. IGF-1 is important in skin repair by stimulating keratinocyte proliferation and migration as well as collagen production by fibroblasts. Its expression is important during wound healing such that retarded healing has been correlated with reduced IGF-1 levels. While local administration of IGF-1 to wound sites enhanced wound closure and stimulated granulation tissue formation, increased IGF-1 receptor expression was reported in chronic wounds and in hypertrophic scars. Additionally, IGF-1 stimulation was associated with increased invasive capacity of keloid fibroblasts. Systemic delivery of IGF-1 also caused hyperglycemia, electrolyte imbalance, and edema. Therefore, it is desirable to have slightly elevated but not over elevated IGF-1 by a treatment modality. TGF-β also is important in skin would healing; however, it is considered a pro-fibrotic growth factor and increased levels of TGF-β or prolonged presence has been identified as causing hypertrophic scaring.

Figure 11A:
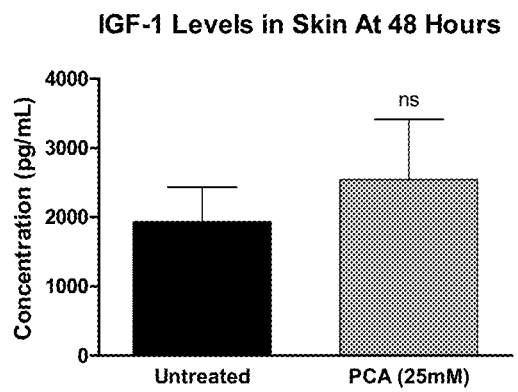
FIG. 11A shows the results of a rodent back skin study to determine the effects of PCA and C3G on the local growth hormones in untreated skin wounds of rodents. A concentration of 25 mM PCA increased local growth hormone levels of IGF-1 at the site of the untreated skin wound.
Figure 11B:
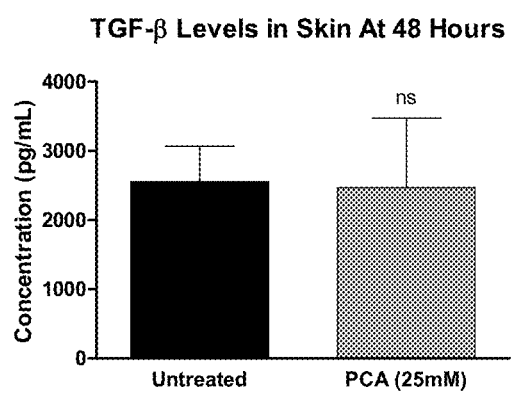
FIG. 11B shows the results of a rodent back skin study to determine the effects of PCA and C3G on the local growth hormones in untreated skin wounds of rodents. A concentration of 25 mM PCA increased local growth hormone levels of TGF-Beta at the site of the untreated skin wound.
Figure 11C:
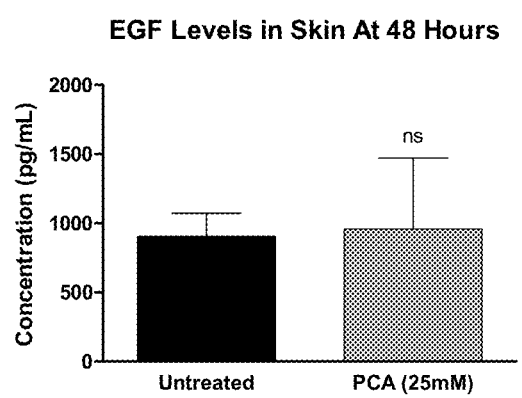
FIG. 11C shows the results of a rodent back skin study to determine the effects of PCA and C3G on the local growth hormones in untreated skin wounds of rodents. A concentration of 25 mM PCA increased local growth hormone levels of EGF at the site of the untreated skin wound.
Figure 12:
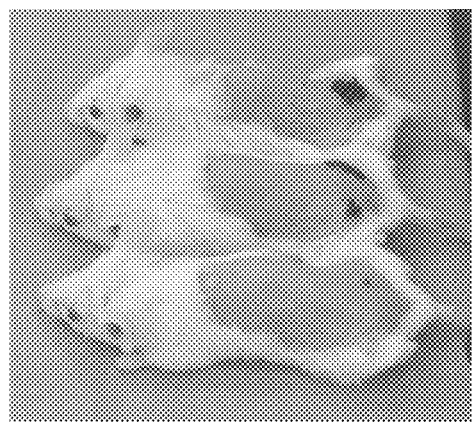
FIG. 12A is a photographic image of rodents treated with a topical solution of C3G (28%); at an acidic pH, this solution maintains a purple or red color and quickly metabolized at elevated pH levels, the C3G changes to a pink or even clear color. In mouse model experiments, however, as observed in the image, the purple color of C3G remained on the rodent wound surface scar, thus indicating the pH remained acidic on the wound surface. The C3G material on the surface was confirmed by subsequent histology.
FIG. 12B is a photographic image of tissue from a study utilizing the homogenized wound tissue method used in this study, whereby the purple color indicates that the wound probably retained an acidic pH.
Figure 12:
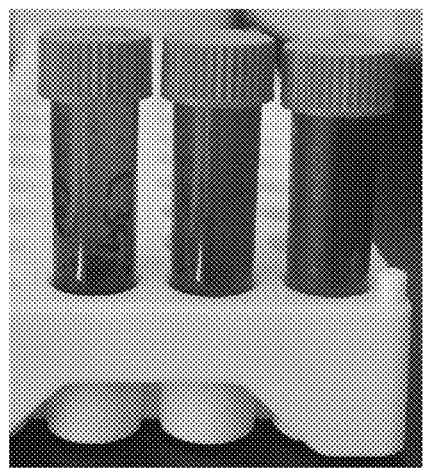

Referring to FIGS. 11-13, tests were performed on rodent skin to explore the effects of PCA on the local growth hormones in rodent skin. A concentration of 25 mM PCA increased local growth hormone levels at the site of the untreated skin wound. In particular, FIG. 11 demonstrates that a single reagent or compound would optimize local growth hormones to promote healing without scarring. Approximately 25 mM PCA was the optimal reagent and dose. As demonstrated in FIG. 13, optimization is possible using the compositions of the present invention. In FIG. 13, all three local growth hormones were lowered in the simulated clinical pathological environment (stripped and infected); however, the lowering of these hormones was not to the extent of absences. Hence, the necessary IGF-1 is still above the controls in this environment; however, the scar forming properties of the other two hormones have been markedly reduced. Therefore, optimization of local growth hormones is achieved. In FIG. 13, the optional concentration of PCA was confirmed as 25 mM PCA in this situation and environment, meaning local growth hormone growth levels were optimized at this dosage such that IGF-1 as moderately elevated while TGF-β and EGF levels were decreased. This is important to promote wound healing while preventing potential scarring.

What is claimed is:

1. A method of treating a biofilm bacterial infection on a surface of an implant or a surface of a patient suspected of having a biofilm bacterial infection, the method comprising:
removing a biofilm-forming bacteria by a minimally invasive technique comprising needle aspiration or an application of ultrasound or both to determine a presence of a biofilm around or on the surface of the implant or surface of the patient, wherein the minimally invasive technique dislodges the removed biofilm-forming bacteria from the biofilm colony and
inhibiting or destroying the biofilm colony and all biofilm-forming bacteria on or around the surface of the implant in the patient or surface of the patient by administering a composition comprising protocatechuic acid or 2,4,6-trihydroxybenzaldehyde or a mixture or combination thereof or administering pure crystals or a powder of protocatechuic acid or 2,4,6-trihydroxybenzaldehyde or a mixture or combination thereof in an amount effective to inhibit or destroy the biofilm on or about the surface of the implant in the patient or the surface of the patient.

2. The method of claim 1, wherein the ultrasound is applied at a frequency and power sufficient to dislodge the biofilm-forming bacteria off the surface of the implant in a patient or the surface of the patient.

3. The method of claim 1, wherein the minimally invasive technique is needle aspiration.

4. The method of claim 1, wherein the minimally invasive technique is needle aspiration and application of ultrasound.

5. The method of claim 1, wherein the ultrasound is applied prior to performing a first needle aspiration.

6. The method of claim 1, wherein the ultrasound is applied after performing a first needle aspiration.

7. The method of claim 1, wherein the surface of the patient is a closed wound, intact skin or skin having a sinus track.

8. The method of claim 1 wherein the implant is a medical device, a medical or surgical implant, total joint prosthesis, a catheter, a dental implant, or a heart or vascular graft.

9. The method of claim 1, wherein a presence of the biofilm on the surface of the implant in the patient or the surface of the patient in previously negative tests for a biofilm-forming bacteria following needle aspiration requires application of ultrasound to dislodge the biofilm colony and biofilm-forming bacteria for confirmation of the presence of the biofilm on the surface of the implant in the patient or surface of the patient.

10. The method of claim 1, wherein the ultrasound is applied by a transcutaneous probe, external stimulation, or lithotripsy.

11. The method of claim 1, wherein a presence of the biofilm on the surface is determined by a needle aspiration prior to the application of the composition or the crystals.

12. The method of claim 1, wherein the biofilm comprises a biofilm-forming bacteria selected from *Pseudomonas aeruginosa* and Methicillin-resistant *Staphylococcus aureus*.

13. The method of claim 1, wherein the composition is a solution comprising protocatechuic acid or 2,4,6-trihydroxybenzaldehyde or a mixture or combination thereof.

14. The method of claim 13, wherein the solution comprises about 0.25% to about 50% by weight of protocatechuic acid or 2,4,6-trihydroxybenzaldehyde or a mixture or combination thereof.

15. The method of claim 14, wherein the solution comprises about 20% to about 30% by weight of protocatechuic acid or 2,4,6-trihydroxybenzaldehyde or a mixture or combination thereof.

16. The method of claim 1, wherein the composition, powder, or the crystals is administered once.

17. The method of claim 1, wherein the composition, powder, or crystals is administered continuously, hourly, daily, weekly, or monthly.

18. The method of claim 1, wherein ultrasound is applied to or near the surface of the implant or surface of the patient having the biofilm bacterial infection to dislodge the biofilm colony and facilitate release of a biofilm-forming bacteria from the surface.

19. The method of claim 1, wherein an aspirate obtained from performing the needle aspiration is cultured to determine if any biofilm-forming bacteria are present, thereby indicating a presence of the biofilm bacterial infection on the surface of the implant or the surface of the patient.

20. The method of claim 1, wherein an aspirate obtained from performing the needle aspiration is cultured to determine if any biofilm forming bacteria are present on the surface of the implant or the surface of the patient following administration of the composition or the crystals.

21. The method of claim 1, wherein the ultrasound is applied at a frequency of about 10 kHz to about 60 kHz.

22. The method of claim 1, wherein the ultrasound is applied at a power density of about 0.1 W/cm$^2$ to about 0.5 W/cm$^2$.

23. The method of claim 1, wherein the ultrasound is applied at a frequency of about 40 kHz and a power density of about 0.22 W/cm$^2$.

24. The method of claim 1, wherein the ultrasound is applied percutaneously and transcutaneously.

25. The method of claim 1, wherein the surface is further washed with a physiologically compatible solution to facilitate release of a biofilm-forming bacteria.

26. The method of claim 1, wherein the surface is washed with a composition comprising an anti-microbial peptide.

27. A method of treating a biofilm bacterial infection on a surface of an implant or a surface of a patient suspected of having a biofilm bacterial infection, the method comprising:
 a) performing a needle aspiration to determine a presence of a biofilm-forming bacteria around or on the surface of the implant or surface of the patient;
 b) culturing the biofilm-forming bacteria obtained from the needle aspiration to determine a presence of the biofilm-forming bacteria around or on the surface of the implant or surface of the patient;
 c) if the culture is negative, then an ultrasound is applied to dislodge the biofilm colony and biofilm-forming bacteria from the surface of the implant or the surface of the patient;
 d) if the culture is identified as positive, then administering to a surrounding space in proximity of the surface of the implant or the surface of a patient a solution comprising protocatechuic acid or 2,4,6-trihydroxybenzaldehyde or a mixture or combination thereof in an amount of about 0.25% to about 50% by weight or administering crystals of protocatechuic acid or 2,4,6-trihydroxybenzaldehyde or a mixture or combination thereof, which is effective to inhibit or destroy the biofilm colony and all biofilm-forming bacteria on the surface of the implant or the surface of the patient; and
 e) optionally applying ultrasound prior to performing the needle aspiration to dislodge the biofilm colony and facilitate release of a biofilm forming bacteria from the surface;
 wherein the surface of the patient is a closed wound, intact skin or skin having minimal exposure with a fistula; and
 wherein the implant is a medical device, a medical or surgical implant, a dental implant, total joint prosthesis, a catheter, or a heart or vascular graft.

* * * * *